US011975194B2

(12) United States Patent
Grill et al.

(10) Patent No.: US 11,975,194 B2
(45) Date of Patent: *May 7, 2024

(54) NON-REGULAR ELECTRICAL STIMULATION PATTERNS FOR IMPROVED EFFICIENCY IN TREATING PARKINSON'S DISEASE

(71) Applicant: Duke University, Durham, NC (US)

(72) Inventors: Warren M. Grill, Chapel Hill, NC (US); David T. Brocker, Alexandria, VA (US); Merrill Birdno, Flagstaff, AZ (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,909

(22) Filed: Oct. 30, 2017

(65) Prior Publication Data

US 2018/0064944 A1  Mar. 8, 2018

Related U.S. Application Data

(63) Continuation of application No. 13/919,860, filed on Jun. 17, 2013, now Pat. No. 9,802,046, which is a (Continued)

(51) Int. Cl.
*A61N 1/36* (2006.01)
*A61N 1/05* (2006.01)

(52) U.S. Cl.
CPC ..... *A61N 1/36067* (2013.01); *A61N 1/36082* (2013.01); *A61N 1/36178* (2013.01); *A61N 1/0534* (2013.01); *A61N 1/36196* (2013.01)

(58) Field of Classification Search
CPC ............ A61N 1/36067; A61N 1/36082; A61N 1/36178; A61N 1/0534; A61N 1/36196
(Continued)

(56) References Cited

U.S. PATENT DOCUMENTS 3,833,005 A   9/1974   Wingrove
4,338,945 A   7/1982   Kosugi et al.
(Continued)

FOREIGN PATENT DOCUMENTS

CN   86102850   11/1987
EP    1145735   10/2001
(Continued)

OTHER PUBLICATIONS

Extended European Search Report for Application 13875748.9 PCT/US2013046183, dated Mar. 9, 2016, European Patent Office, Germany.
(Continued)

*Primary Examiner* — Tammie K Marlen
(74) *Attorney, Agent, or Firm* — McDonald Hopkins LLC

(57) ABSTRACT

Systems and methods for stimulation of neurological tissue generate stimulation trains with temporal patterns of stimulation, in which the interval between electrical pulses (the inter-pulse intervals) changes or varies over time. Compared to conventional continuous, high rate pulse trains having regular (i.e., constant) inter-pulse intervals, the non-regular (i.e., not constant) pulse patterns or trains that embody features of the invention provide a lower average frequency. The systems and methods for stimulation of neurological tissue may be used to increase the efficacy of treatment in patients with Parkinson's Disease.

9 Claims, 35 Drawing Sheets

Related U.S. Application Data continuation-in-part of application No. 13/770,731, filed on Feb. 19, 2013, now Pat. No. 8,923,981, which is a continuation-in-part of application No. 12/587,295, filed on Oct. 5, 2009, now Pat. No. 8,447,405.

(60) Provisional application No. 61/660,672, filed on Jun. 15, 2012, provisional application No. 61/600,264, filed on Feb. 17, 2012, provisional application No. 61/102,575, filed on Oct. 3, 2008.

(58) Field of Classification Search
USPC .......................................................... 607/45
See application file for complete search history.

(56) References Cited

U.S. PATENT DOCUMENTS

| | | | |
|---|---|---|---|
| 4,979,507 A | 12/1990 | Heinz | |
| 5,018,524 A | 5/1991 | Gu et al. | |
| 5,073,544 A | 12/1991 | Seto | |
| 5,095,904 A | 3/1992 | Seligman et al. | |
| 5,184,616 A | 7/1993 | Weiss | |
| 5,226,413 A | 7/1993 | Bennett | |
| 5,485,851 A | 1/1996 | Erickson | |
| 5,716,377 A | 2/1998 | Rise et al. | |
| 5,724,985 A | 3/1998 | Snell | |
| 6,066,163 A | 5/2000 | Sasha | |
| 6,212,432 B1 | 4/2001 | Matsuura | |
| 6,560,487 B1 | 5/2003 | McGraw et al. | |
| 6,560,490 B2 | 5/2003 | Grill et al. | |
| 6,738,668 B1 | 5/2004 | Mouchawar | |
| 6,879,860 B2 | 4/2005 | Wakefield | |
| 6,934,580 B1 | 8/2005 | Osorio | |
| 6,944,501 B1 | 9/2005 | Pless | |
| 7,010,351 B2 | 3/2006 | Firlik et al. | |
| 7,191,014 B2 | 3/2007 | Kobayashi et al. | |
| 7,321,796 B2 | 1/2008 | Fink | |
| 7,483,747 B2 | 1/2009 | Gilner et al. | |
| 7,949,397 B1 | 5/2011 | Wenzel | |
| 7,970,477 B2 | 6/2011 | Loeb | |
| 8,073,544 B2 | 12/2011 | Pless | |
| 8,355,789 B2 | 1/2013 | Werder et al. | |
| 8,447,405 B2 | 5/2013 | Grill et al. | |
| 8,694,106 B2 | 4/2014 | Pless | |
| 8,798,755 B2 | 8/2014 | Grill et al. | |
| 8,923,981 B2 * | 12/2014 | Grill, Jr. | A61N 1/36128 607/70 |
| 9,089,708 B2 | 7/2015 | Grill | |
| 9,242,095 B2 * | 1/2016 | Grill, Jr. | A61N 1/36128 |
| 9,259,579 B2 | 2/2016 | Grill et al. | |
| 9,572,988 B2 | 2/2017 | Grill | |
| 9,744,363 B2 | 8/2017 | Grill | |
| 9,802,046 B2 * | 10/2017 | Grill | A61N 1/36082 |
| 10,086,204 B2 | 10/2018 | Grill | |
| 10,086,205 B2 | 10/2018 | Grill | |
| 2002/0077670 A1 | 6/2002 | Archer | |
| 2002/0177882 A1 | 11/2002 | DiLorenzo | |
| 2003/0135248 A1 | 7/2003 | Stypulkowski | |
| 2004/0158298 A1 | 8/2004 | Gliner et al. | |
| 2004/0243192 A1 | 12/2004 | Hepp | |
| 2004/0249422 A1 | 12/2004 | Gliner et al. | |
| 2005/0060009 A1 | 3/2005 | Goetz | |
| 2005/0222641 A1 | 10/2005 | Pless | |
| 2005/0228453 A1 | 10/2005 | Havel | |
| 2005/0228461 A1 * | 10/2005 | Osorio | A61B 5/0484 607/45 |
| 2006/0015153 A1 * | 1/2006 | Gliner | A61N 1/3606 607/45 |
| 2006/0017749 A1 | 1/2006 | McIntyre | |
| 2006/0111759 A1 | 5/2006 | Hoyme | |
| 2006/0212089 A1 | 9/2006 | Tass | |
| 2007/0067004 A1 | 3/2007 | Boveja | |
| 2007/0198066 A1 | 8/2007 | Greenberg | |
| 2007/0288064 A1 | 12/2007 | Butson et al. | |
| 2008/0045775 A1 | 2/2008 | Lozano | |
| 2009/0036949 A1 | 2/2009 | Kokones | |
| 2009/0082640 A1 | 3/2009 | Kovach | |
| 2009/0110958 A1 | 4/2009 | Hyde | |
| 2009/0131993 A1 | 5/2009 | Rousso et al. | |
| 2009/0264954 A1 | 10/2009 | Rise | |
| 2010/0042194 A1 | 2/2010 | Ayal | |
| 2010/0121407 A1 | 5/2010 | Pfaff | |
| 2010/0121416 A1 | 5/2010 | Lee | |
| 2010/0152807 A1 | 7/2010 | Grill et al. | |
| 2010/0312303 A1 | 12/2010 | York | |
| 2010/0331916 A1 | 12/2010 | Parramon | |
| 2011/0093041 A1 | 4/2011 | Straka et al. | |
| 2011/0106213 A1 | 5/2011 | Davis | |
| 2011/0184486 A1 | 7/2011 | De Ridder | |
| 2011/0196441 A1 | 8/2011 | Ryu | |
| 2011/0270348 A1 | 11/2011 | Goetz | |
| 2012/0004707 A1 | 1/2012 | Lee | |
| 2012/0016435 A1 | 1/2012 | Rom | |
| 2012/0290041 A1 | 11/2012 | Kim | |
| 2013/0006330 A1 | 1/2013 | Wilder | |
| 2013/0102919 A1 | 4/2013 | Schiff | |
| 2013/0231715 A1 | 9/2013 | Grill | |
| 2013/0345773 A1 | 12/2013 | Grill et al. | |
| 2014/0257428 A1 | 9/2014 | Zhu | |
| 2014/0353944 A1 | 12/2014 | Grill et al. | |
| 2017/0361099 A1 | 12/2017 | De Ridder | |
| 2018/0064944 A1 | 3/2018 | Grill | |

FOREIGN PATENT DOCUMENTS

| | | |
|---|---|---|
| EP | 2766087 | 8/2014 |
| JP | 2008506464 | 3/2008 |
| WO | 2006019764 | 2/2006 |
| WO | 2010039274 | 4/2010 |
| WO | 2014130071 | 8/2014 |

OTHER PUBLICATIONS

International Search Report and the Written Opinion of the International Searching Authority, PCT/US2013/046183, Duke University, dated Oct. 4, 2013.

International Search Report and the Written Opinion of the International Searching Authority, PCT/US2012/059787, Duke University, dated Jan. 4, 2013.

International Preliminary Examination Report, PCT/US2009/05459, Duke University, dated Jan. 11, 2011.

International Search Report and the Written Opinion of the International Searching Authority, PCT/US2009/05459, Duke University, dated Dec. 3, 2009.

Extended European Search Report, Application No. 09818122.5-1652/2340078, Duke University, dated Aug. 2, 2013.

Rubin, Jonathan et al., High Frequency Stimulation of the Subthalamic Nucleus Eliminates Pathological Thalamic Rhythmicity in a Computational Model, Journal of Computational Neuroscience, vol. 16, pp. 211-235, 2004.

McIntyre, Cameron et al., Cellular Effects of Deep Brain Stimulation: Model-Based Analysis of Activation and Inhibition, J. Neurophysiol, vol. 91, pp. 1457-1469, 2004.

Birdno, Merrill Jay, Analyzing the Mechanisms of Action of Thalamic Deep Brain Stimulation: Computational and Clinical Studies, Ph. D. Dissertation, Department of Biomedical Engineering, Duke University, Durham, NC, USA, Aug. 2009.

Constantoyannis, Constantine, et al., Tremor Induced by Thalamic Deep Brain Stimulation in Patients with Complex Regional Facial Pain, Movement Disorders, vol. 19, No. 8, pp. 933-936, 2004.

Benabid, Alim et al., Long-term suppression of tremor by chronic stimulation of the ventral intermediate thalamic nucleus, The Lancet, vol. 337, pp. 403-406, Feb. 16, 1991.

Davis, Lawrence, Handbook of Genetic Algorithms, Van Nostrand Reinhold, NY, pp. 1-402, 1991.

Dorval, Alan et al., Deep Brain Stimulation Alleviates Parkinsonian Bradykinesia by Regularizing Pallidal Activity, J. Neurophysiol, vol. 104, pp. 911-921, 2010.

(56) References Cited

OTHER PUBLICATIONS

Fogelson, Noa et al., Frequency dependent effects of subthalamic nucleus stimulation in Parkinson's disease, Neuroscience Letters 382, 5-9, 2005.
Grefenstette, John, Optimization of Control Parameters for Genetic Algorithms, IEEE Transactions on Systems, Man, and Cybernetics, vol. SMC-16, No. 1, pp. 122-128, Jan./Feb. 1986.
Feng, Xiao-jiang et al., Optimal Deep Brain Stimulation of the Subthalamic Nucleus—a Computational Study, Journal of Computational Neuroscience, 23(3):265-282, Jan. 9, 2007.
Grill, W.M. et al., Effect of waveform on tremor suppression and paresthesias evoked by thalamic deep brain stimulation (dbs), Society for Neuroscience Abstract 29, 2003.
Kuncel, Alexis et al., Clinical Response to Varying the Stimulus Parameters in Deep Brain Stimulation for Essential Tremor, Movement Disorders, vol. 21, No. 11, pp. 1920-1928, 2006.
Kupsch, A. et al., The effects of frequency in pallidal deep brain stimulation for primary dystonia, J. Neurol 250:1201-1205, 2003.
Tinnerman, Lars et al., The cerebral oscillatory network of parkinsonian resting tremor, Brain, 126, pp. 199-212, 2003.
Limousin, Patricia et al., Effect on parkinsonian signs and symptoms of bilateral subthalamic nucleus stimulation, The Lancet, vol. 345, pp. 91-95, Jan. 14, 1995.
SA/US, International Search Report and Written Opinion prepared for PCT/US2014/072112, dated Apr. 16, 2015.
International Preliminary Report on Patentability for PCT/US11/38416, dated May 3, 2012.
International Search Report/Written Opinion dated Dec. 7, 2011 in International Patent Application No. PCT/US11/38416.
International Searching Authority, US Patent Office; International Search Report and Written Opinion for PCT/US2014/038809, dated Dec. 15, 2014, 19 pages.
Feng et al. "Toward closed-loop optimization of deep brain stimulation for Parkinson's disease: concepts and lessons from a computational model." J. Neural Eng. 4 (2007) L14-L21. Feb. 23, 2007.
So et al. "Relative contributions of local cell and passing fiber activation and silencing to changes in thalamic fidelity luring deep brain stimulation and lesioning: a computational modeling study". Comput Neurosci (2012) 32:499-519. Oct. 5, 2011.
Kent et al. "Instrumentation to Record Evoked Potentials for Closed-Loop Control of Deep Brain Stimulation". Conf Proc IEEE Eng Med Biol Soc. 2011; 2011: 6777-6780. doi:10.1109/IEMBS.2011.6091671.
Dorval et al. "Deep Brain Stimulation that Abolishes Parkinsonian Activity in Basal Ganglia Improves Thalamic Relay Fidelity in a Computational Circuit". Conf Proc IEEE Eng Med Biol Soc. 2009; 1: 4230. doi:10.11091EMB5.2009.5333611.
Brocker, David. et al., Improved Efficacy of Temporally Non-Regular Deep Brain Stimulation in Parkinson's Disease, Department of Biomedical Engineering, Duke University, Durham NC 27708-0281, pp. 1-34, 2012.
European Patent Office, Supplementary European Search Report, EP14874436, dated Jan. 17, 2018.
European Patent Office, European Search Report, EP 17001653, dated Jan. 4, 2018.
European Patent Office, Extended European Search Report for U.S. Appl. No. 20/175,204, dated Aug. 27, 2020, 8 pages.

\* cited by examiner

Single Crossover

NON-REGULAR ELECTRICAL STIMULATION PATTERNS FOR IMPROVED EFFICIENCY IN TREATING PARKINSON'S DISEASE

CROSS-REFERENCE TO RELATED APPLICATION

This application is a continuation of co-pending U.S. patent application Ser. No. 13/919,860, filed Jun. 17, 2013, and entitled "Non-Regular Electrical Stimulation Patterns for Improved Efficiency in Treating Parkinson's Disease," now granted as U.S. Pat. No. 9,802,046, which is a continuation in part of co-pending U.S. patent application Ser. No. 13/770,731, filed Feb. 19, 2013, and entitled "Non-Regular Electrical Stimulation Patterns for Treating Neurological Disorders," now granted as U.S. Pat. No. 8,923,981, which claimed priority to U.S. Provisional Application Ser. No. 61/600,264, entitled "Non-Regular Electrical Stimulation Patterns for Treating Neurological Disorders," filed on Feb. 17, 2012. U.S. patent application Ser. No. 13/770,731 is also a continuation in part of U.S. patent application Ser. No. 12/587,295, filed Oct. 5, 2009, and entitled "Non-Regular Electrical Stimulation Patterns for Treating Neurological Disorders," now granted as U.S. Pat. No. 8,447,405, which claimed the benefit of U.S. Provisional Patent Application Ser. No. 61/102,575, filed Oct. 3, 2008, and entitled "Stimulation Patterns For Treating Neurological Disorders Via Deep Brain Stimulation," all of which are hereby incorporated in their entirety by reference. U.S. patent application Ser. No. 13/919,860 also claimed the benefit of U.S. Provisional Patent Application Ser. No. 61/660,672, filed Jun. 15, 2012, and entitled "Improved Efficacy of Temporally Non-Regular Deep Brain Stimulation in Parkinson's Disease," which is hereby incorporated in its entirety by reference.

FIELD OF INVENTION

This invention relates to systems and methods for stimulating nerves in animals, including humans.

BACKGROUND

Deep Brain Stimulation (DBS) has been found to be successful in treating a variety of brain-controlled disorders, including movement disorders. Generally, such treatment involves placement of a DBS type lead into a targeted region of the brain through a burr hole drilled in the patient's skull, and the application of appropriate stimulation through the lead to the targeted region.

Presently, in DBS, beneficial (symptom-relieving) effects are observed primarily at high stimulation frequencies above 100 Hz that are delivered in stimulation patterns or trains in which the interval between electrical pulses (the inter-pulse intervals) is constant over time. The beneficial effects of DBS on motor symptoms are only observed at high frequencies, while low frequency stimulation has generally been thought to exacerbate symptoms. For instance, thalamic DBS at less than or equal to 50 Hz has been shown to increase tremor in patients with essential tremor. Similarly, 50 Hz DBS has been shown to produce or induce tremor in pain patients receiving simulation of the ventral posterior medial nucleus of the thalamus (VPM), but the tremor disappears when the frequency is increased. Likewise, DBS of the subthalamic nucleus (STN) at 10 Hz has been shown to worsen akinesia in patients with Parkinson's Disease (PD), while DBS at 130 Hz leads to significant improvement in motor function. Similarly, relatively high frequency stimulation of the globus pallidus (GP) at or above 130 Hz has been shown to improve dystonia, whereas stimulation at either 5 or 50 Hz may lead to significant worsening.

Model studies also indicate that the masking of pathological burst activity occurs only with sufficiently high stimulation frequencies. Responsiveness of tremor to changes in DBS amplitude and frequency are strongly correlated with the ability of applied stimuli to mask neuronal bursting.

Although effective, conventional high frequency stimulation generates stronger side-effects than low frequency stimulation, and the therapeutic window between the voltage that generates the desired clinical effect(s) and the voltage that generates undesired side effects decreases with increasing frequency. Precise lead placement therefore becomes important. Further, high stimulation frequencies increase power consumption. The need for higher frequencies and increased power consumption shortens the useful lifetime and/or increases the physical size of battery-powered implantable pulse generators. The need for higher frequencies and increased power consumption requires a larger battery size, and/or frequent charging of the battery, if the battery is rechargeable, or replacement of the battery if it is not rechargeable.

The motor symptoms of PD are treated with high frequency deep brain stimulation (OBS) in the internal segment of the globus pallidus (GPi) or subthalamic nucleus (STN). The efficacy of DBS for PD is sensitive to the stimulation parameters, with high frequency (>100 Hz) DBS being more efficacious than low frequency (<100 Hz) stimulation. The frequency-dependent efficacy of DBS is a key element for the proposed mechanisms of OBS, including: stimulation-induced regularization of pathological neuronal activity, and silencing of the stimulated neurons. The efficacy of OBS is also dependent on the amplitude, polarity, pulse width, and pattern of stimulation. However, the temporal pattern of stimulation stands out as a potentially important parameter space that has not been fully explored.

Non-regular temporal patterns of stimulation provide a means to probe the mechanisms of OBS, and could potentially be used to expand the therapeutic efficacy of DBS. Random patterns of stimulation are less effective at suppressing motor symptoms than regular stimulation in patients with essential tremor (ET) and PD. In patients with ET, non-regular stimulation patterns are less effective at suppressing tremor than temporally regular stimulation because sufficiently long gaps in the stimulation train allow pathological activity to propagate through the stimulated nucleus. However, the features of non-regular stimulation patterns that influence clinical efficacy in PD are unknown.

SUMMARY

The invention provides stimulation patterns or trains with different temporal patterns of stimulation than conventional stimulation trains. The invention also provides methodologies to identify and characterize stimulation patterns or trains that produce desired or greater relief of symptoms and/or reducing the average stimulation frequency. The invention also provides a neural stimulation device to transmit stimulation patterns or trains for the improved efficacy in treating PD.

According to one aspect of the invention, the intervals between stimulation pulses in a pulse pattern or train (in shorthand called "the inter-pulse intervals") is not constant over time, but changes or varies over time. These patterns or trains are consequently called in shorthand "non-regular." According to this aspect of the invention, the non-regular (i.e., not constant) pulse patterns or trains may provide a lower average frequency for a given pulse pattern or train, compared to conventional continuous, high rate pulse trains having regular (i.e., constant) inter-pulse intervals. The non-regular stimulus patterns or trains may make possible an increase in the efficacy of stimulation by reducing the intensity of side effects; by increasing the dynamic range between the onset of the desired clinical effect(s) and side effects (and thereby reducing sensitivity to the position of the lead electrode); and may decrease power consumption, thereby providing a longer useful battery life and/or a smaller implantable pulse generator, allowing battery size reduction and/or, for rechargeable batteries, longer intervals between recharging.

The non-regular stimulation patterns or trains can be readily applied to deep brain stimulation, to treat a variety of neurological disorders, such as PD, movement disorders, epilepsy, and psychiatric disorders such as obsessive-compulsion disorder and depression. The non-regular stimulation patterns or trains can also be readily applied to other classes electrical stimulation of the nervous system including, but not limited to, cortical stimulation, spinal cord stimulation, and peripheral nerve stimulation (including sensory and motor), to provide the attendant benefits described above and to treat diseases such as but not limited to PD, essential tremor, movement disorders, dystonia, epilepsy, pain, psychiatric disorders such as obsessive compulsive disorder, depression, and Tourette's Syndrome.

According to another aspect of the invention, systems and methodologies make it possible to determine the effects of the temporal pattern of DBS on simulated and measured neuronal activity, as well as motor symptoms in both animals and humans. The methodologies make possible the qualitative determination of the temporal features of stimulation trains.

The systems and methodologies described herein employ a genetic algorithm, coupled to a computational model of DBS of the STN, to develop non-regular patterns of stimulation that produced efficacy (as measured by a low error function, E often at lower stimulation frequencies, F than conventional regular deep brain stimulation. The error function, E, is a quantitative measure from the model which assesses how faithfully the thalamus transmitted motor commands that are generated by inputs from the cortex. A very high correlation exists between E and symptoms in persons with PD, and therefore E is a valid predictor for the efficacy of a stimulation train in relieving symptoms.

Previous efforts sought to design stimulation trains that minimized the total current injection. The systems and methodologies disclosed herein include an objective function that maximizes therapeutic benefit (by minimizing the error function) and may improve stimulation efficiency (by reducing the average stimulation frequency below that of the optimal conventional (regularly timed) stimulation), using a model of the STN, GPi, and GPe (external globus pallidus) that reproduces the frequency tuning of symptom reduction that has been documented clinically. In contrast, a first model showed, incorrectly, symptom reduction with regular, low frequency stimulation. The inventors have identified novel non-regular temporal patterns of stimulation, while the first model identified regular low frequency (~10 Hz) trains that previous clinical work has demonstrated to be ineffective.

A neural stimulation device may include a pulse generator configured to transmit a first temporal pattern of stimulation for application to neurological tissue having a first non-regular pulse train, the first non-regular pulse train including a first plurality of single pulses (first singlets) and embedded first multiple pulse groups (first n-lets), with non-regular inter-pulse intervals between the first singlets and first n-lets, as well as non-regular inter-pulse intervals within the first n-lets themselves. The pulse generator may also be configured to transmit a second temporal pattern of stimulation for application to neurological tissue having a second non-regular pulse train, the second non-regular pulse train including a second plurality of single pulses (second singlets) and embedded second multiple pulse groups (second n-lets), with non-regular inter-pulse intervals between second singlets and second n-lets, as well as non-regular inter-pulse intervals within the second n-lets themselves, the second temporal pattern adapted from applying a model-based optimization technique after application of the first temporal pattern of stimulation.

A method for stimulation of a targeted neurological tissue region may include the steps of applying electrical current to a targeted neurological tissue region of an animal using a pulse generator according to a first non-regular pulse train including a first plurality of single pulses (first singlets) and embedded first multiple pulse groups (first n-lets), with non-regular inter-pulse intervals between the first singlets and first n-lets, as well as non-regular inter-pulse intervals within the first n-lets themselves, and analyzing results of the first non-regular pulse train. The method may further include the steps of applying a model-based optimization technique determining a second non-regular pulse trains including a second plurality of single pulses (second singlets) and embedded second multiple pulse groups (second n-lets), with non-regular inter-pulse intervals between second singlets and second n-lets, as well as non-regular inter-pulse intervals within the second n-lets themselves, and applying electrical current to the targeted neurological tissue region of the animal using the pulse generator according to the second non-regular pulse train.

The neural stimulation device of the invention may include a pulse generator configured to apply a first non-regular pulse train, having at least one first singlet spaced apart by a first inter-pulse singlet interval and at least one first n-let having, for each n-let, two or more pulses spaced apart by a first inter-pulse interval that is less than the first singlet inter-pulse interval. The pulse generator may also be configurable to apply a second non-regular pulse train, having at least one second singlet spaced apart by a second inter-pulse singlet interval and at least one second n-let having, for each n-let, two or more pulses spaced apart by a second inter-pulse interval that is less than the second singlet inter-pulse interval, the second non-regular pulse trail based upon an analysis of the first non-regular pulse train. The neural stimulation device may also include at least one input configured to operatively connect with at least one electrode to record neural activity (e.g., Beta Band Power).

The neural stimulation device may be used to apply different temporal patterns of stimulation to humans with PD to determine which features of non-regular stimulation cause it to be less effective than temporally regular stimulation. Certain non-regular patterns of stimulation significantly improve performance on a simple motor task as compared to regular stimulation. A computational model of DBS in the basal ganglia shows that efficacy of various stimulation patterns relate to their ability to suppress pathological oscillations in the beta frequency range. These results highlight the potential importance of this heretofore unexplored parameter space as a means to enhance the efficacy of DBS for the treatment of PD.

BRIEF DESCRIPTION OF THE DRAWINGS

Operation of the invention may be better understood by reference to the detailed description taken in connection with the following illustrations, wherein.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
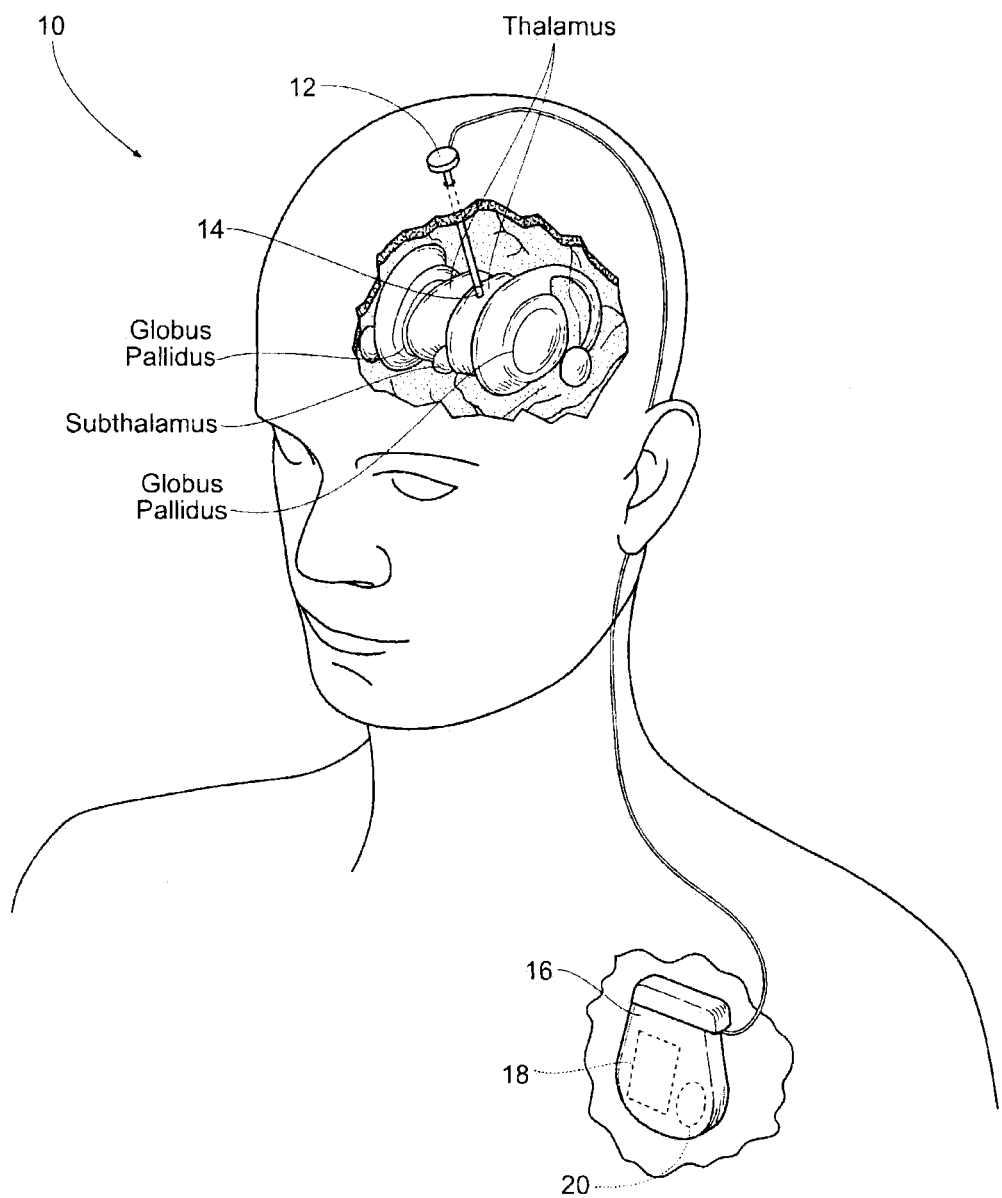
FIG. 1 is an anatomic view of a system for stimulating tissue of the central nervous system that includes an lead implanted in brain tissue coupled to a pulse generator that is programmed to provide non-regular (i.e., not constant) pulse patterns or trains, in which the interval between electrical pulses (the inter-pulse intervals) changes or varies over time.

FIG. 1 is a system 10 for stimulating tissue of the central nervous system. The system may include a lead 12 placed in a desired position in contact with central nervous system tissue. In the illustrated embodiment, the lead 12 may be implanted in a region of the brain, such as the thalamus, subthalamus, or globus pallidus for the purpose of deep brain stimulation. However, it should be understood, the lead 12 may be implanted in, on, or near the spinal cord; or in, on, or near a peripheral nerve (sensory or motor) for the purpose of selective stimulation to achieve a therapeutic purpose.

The distal end of the lead 12 may carry one or more electrodes 14 to apply electrical pulses to the targeted tissue region. The electrical pulses may be supplied by a pulse generator 16 coupled to the lead 12.

In the illustrated embodiment, the pulse generator 16 may be implanted in a suitable location remote from the lead 12, e.g., in the shoulder region. It should be appreciated, however, that the pulse generator 16 may be placed in other regions of the body, i.e., implanted in any suitable location, or externally.

When implanted, the case of the pulse generator 16 may serve as a reference or return electrode. Alternatively, the lead 12 may include a reference or return electrode (comprising a bi-polar arrangement), or a separate reference or return electrode may be implanted or attached elsewhere on the body (comprising a mono-polar arrangement).

The pulse generator 16 may include an on-board, programmable microprocessor 18, which carries embedded code. The code may express pre-programmed rules or algorithms under which a desired electrical stimulation waveform pattern or train is generated and distributed to the electrode(s) 14 on the lead 12. According to these programmed rules, the pulse generator 16 may direct the prescribed stimulation waveform patterns or trains through the lead 12 to the electrode(s) 14, which serve to selectively stimulate the targeted tissue region. The code may be preprogrammed by a clinician to achieve the particular physiologic response desired.

In the illustrated embodiment, an on-board battery 20 may supply power to the microprocessor 18. Currently, batteries 20 must be replaced every 1 to 9 years, depending on the stimulation parameters needed to treat a disorder. When the battery life ends, the replacement of batteries requires another invasive surgical procedure to gain access to the implanted pulse generator. As will be described, the system 10 makes possible, among its several benefits, an increase in battery life.

Figure 2:
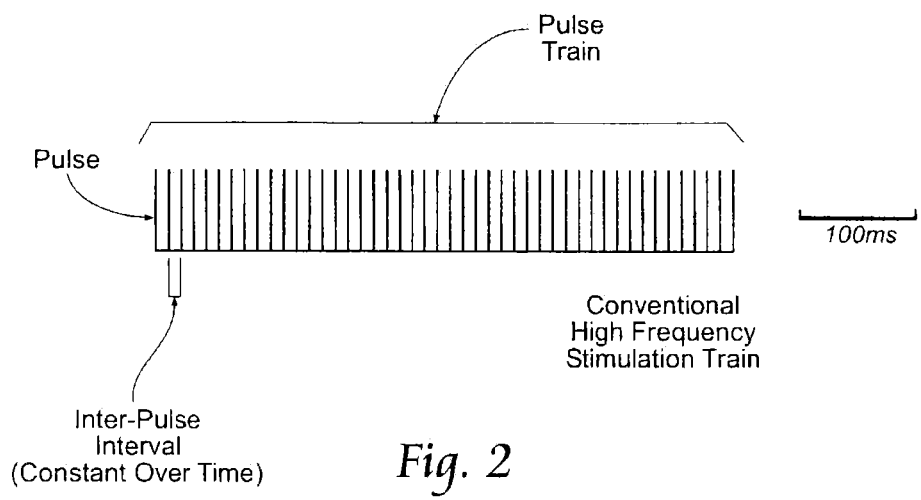
FIG. 2 is a diagrammatic trace that shows a conventional regular high frequency stimulation train, in which the interval between electrical pulses (the inter-pulse intervals) is constant.
Figure 3:
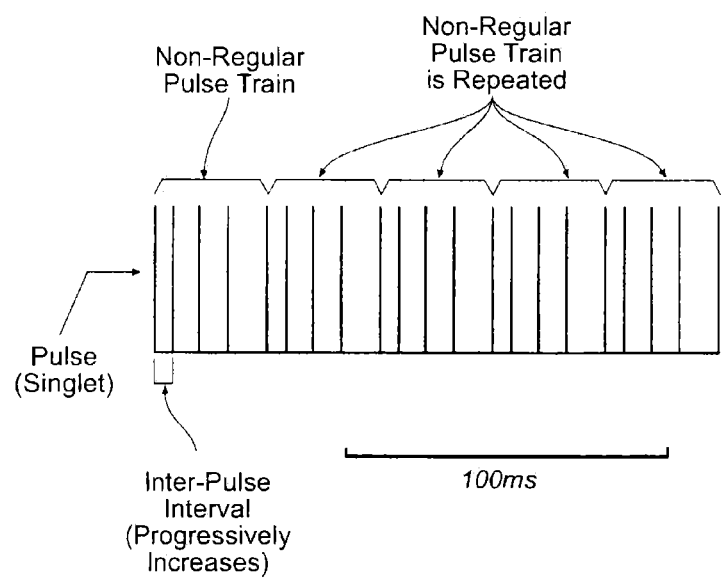
FIG. 3 is a diagrammatic trace showing a representative example of a repeating non-regular pulse pattern or train in which the inter-pulse intervals are linearly cyclically ramped over time.
Figure 4:
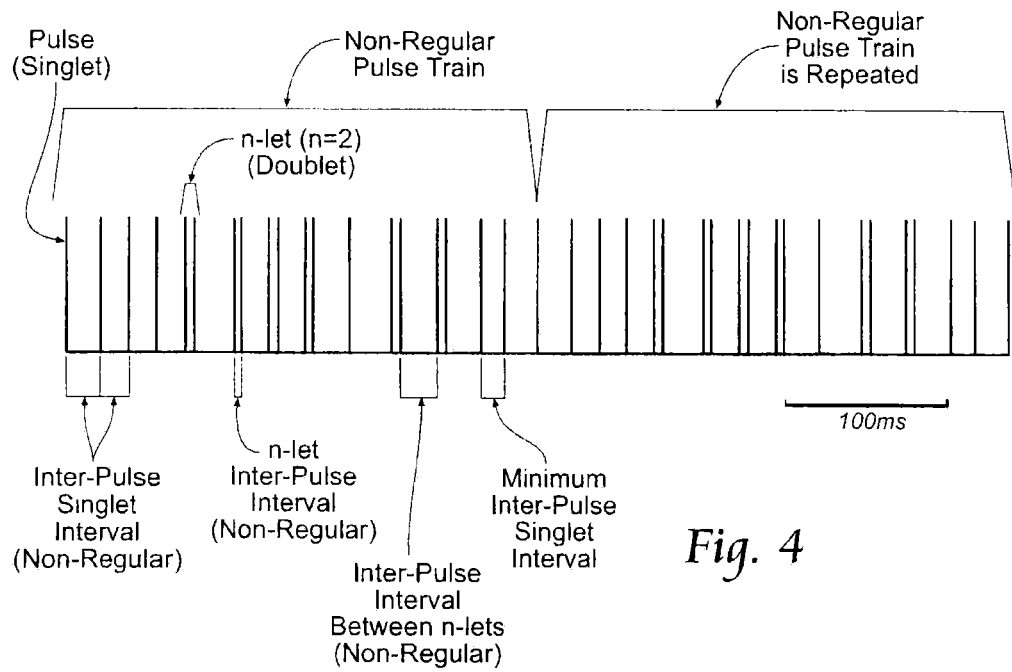
FIGS. 4 and 5 are diagrammatic traces showing other representative examples of repeating non-regular pulse patterns or trains comprising within, a single pulse train, a combination of single pulses (singlets) and embedded multiple pulse groups (n-lets), with non-regular inter-pulse intervals between singlets and n-lets as well as non-regular inter-pulse intervals within the multiple pulse n-lets.
Figure 5:
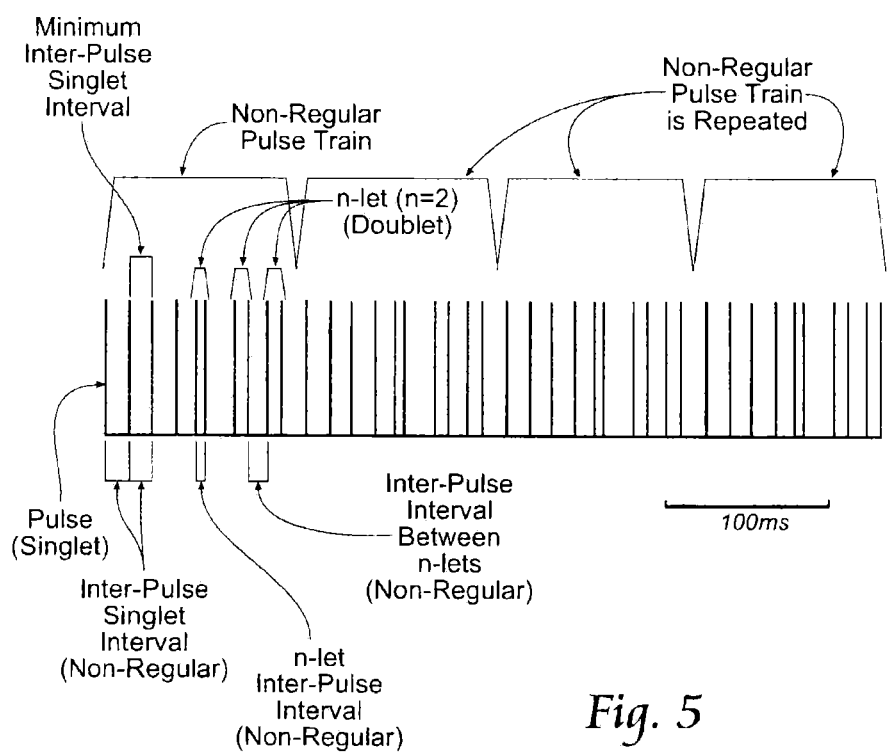

The stimulation waveform pattern or train generated by the pulse generator differs from convention pulse patterns or trains in that the waveform comprises repeating non-regular (i.e., not constant) pulse patterns or trains, in which the interval between electrical pulses (the inter-pulse intervals or IPI) changes or varies over time. Examples of these repeating non-regular pulse patterns or trains are shown in FIGS. 3 to 5. Compared to conventional pulse trains having regular (i.e., constant) inter-pulse intervals (as shown in FIG. 2), the non-regular (i.e., not constant) pulse patterns or trains provide a lower average frequency for a given pulse pattern or train, where the average frequency for a given pulse train (expressed in hertz or Hz) is defined as the sum of the inter-pulse intervals for the pulse train in seconds ($\Sigma_{IPI}$) divided by the number of pulses (n) in the given pulse train, or ($\Sigma_{IPI}$)/n. A lower average frequency makes possible a reduction in the intensity of side effects, as well as an increase in the dynamic range between the onset of the desired clinical effect(s) and side effects, thereby increasing the clinical efficacy and reducing sensitivity to the position of the electrode(s). A lower average frequency brought about by a non-regular pulse pattern or train also leads to a decrease in power consumption, thereby prolonging battery life and reducing battery size.

The repeating non-regular (i.e., not constant) pulse patterns or trains can take a variety of different forms. For example, as will be described in greater detail later, the inter-pulse intervals can be linearly cyclically ramped over time in non-regular temporal patterns (growing larger and/or smaller or a combination of each over time); or be periodically embedded in non-regular temporal patterns comprising clusters or groups of multiple pulses (called n-lets), wherein n is two or more. For example, when n=2, the n-let can be called a doublet; when n=3, the n-let can be called a triplet; when n=4, the n-let can be called a quadlet; and so on. The repeating non-regular pulse patterns or trains can comprise combinations of single pulses (called singlets) spaced apart by varying non-regular inter-pulse intervals and n-lets interspersed among the singlets, the n-lets themselves being spaced apart by varying non-regular inter-pulse intervals both between adjacent n-lets and between the n pulses embedded in the n-let. If desired, the non-regularity of the pulse pattern or train can be accompanied by concomitant changes in waveform and/or amplitude, and/or duration in each pulse pattern or train or in successive pulse patterns or trains.

Each pulse comprising a singlet or imbedded in an n-let in a given train comprises a waveform that can be monophasic, biphasic, or multiphasic. Each waveform possesses a given amplitude (expressed, e.g., in amperes) that can, by way of example, range from 10 μa ($E^{-6}$) to 10 ma ($E^{-3}$). The amplitude of a given phase in a waveform can be the same or differ among the phases. Each waveform also possesses a duration (expressed, e.g., in seconds) that can, by way of example, range from 10 μs ($E^{-6}$) to 2 ms ($E^{-3}$). The duration of the phases in a given waveform can likewise be the same or different. It is emphasized that all numerical values expressed herein are given by way of example only. They can be varied, increased or decreased, according to the clinical objectives.

When applied in deep brain stimulation, it is believed that repeating stimulation patterns or trains applied with non-regular inter-pulse intervals can regularize the output of disordered neuronal firing, to thereby prevent the generation and propagation of bursting activity with a lower average stimulation frequency than required with conventional constant frequency trains, i.e., with a lower average frequency than about 100 Hz, and/or greater treatment efficacy than can otherwise be achieved with conventional constant frequency trains. FIG. 3 shows a representative example of a repeating non-regular pulse pattern or train in which the inter-pulse intervals are linearly cyclically ramped over time. The inter-pulse intervals can vary within a specified range selected based upon clinical objections, e.g., not to exceed 25 ms, or not to exceed 100 ms, or not to exceed 200 ms, to take into account burst responses and subsequent disruption of thalamic fidelity. The non-regular pulse trains repeat themselves for a clinically appropriate period of time, i.e., as long as the treatment is desired and effective.

FIGS. 4 and 5 show other representative examples of repeating non-regular pulse patterns or trains. The pulse trains in FIGS. 4 and 5 comprise within, a single pulse train, a combination of single pulses (singlets) and embedded multiple pulse groups (n-lets), with non-regular inter-pulse intervals between singlets and n-lets, as well as non-regular inter-pulse intervals within the n-lets themselves. The non-regular pulse trains repeat themselves for a clinically appropriate period of time.

The non-regular pulse train can be characterized as comprising one or more singlets spaced apart by a minimum inter-pulse singlet interval and one or more n-lets comprising, for each n-let, two or more pulses spaced apart by an inter-pulse interval (called the "n-let inter-pulse interval") that is less than the minimum singlet inter-pulse interval. The n-let inter-pulse interval can itself vary within the train, as can the interval between successive n-lets or a successive n-lets and singlets. The non-regular pulse trains comprising singlets and n-lets repeat themselves for a clinically appropriate period of time.

In FIG. 4, each pulse train comprises four singlets in succession (with non-regular inter-pulse intervals there between); followed by four doublets in succession (with non-regular inter-doublet pulse intervals there between and non-regular inter-pulse intervals within each n-let); followed by a singlet, three doublets, and a singlet (with non-regular inter-pulse intervals there between and non-regular inter-pulse intervals within each n-let). The temporal pattern of this pulse train repeats itself in succession for a clinically appropriate period of time. The non-regular temporal pulse pattern shown in FIG. 4 has an average frequency of 67.82 Hz without loss of efficacy, as is demonstrated in the following Example, Batch 17.

In FIG. 5, each pulse train comprises four singlets in succession (with non-regular inter-pulse intervals there between); followed by three doublets in succession (with non-regular inter-doublet pulse intervals there between and non-regular inter-pulse intervals within each n-let). The temporal pattern of this pulse train repeats itself in succession for a clinically appropriate period of time. The non-regular temporal pulse pattern shown in FIG. 5 has an average frequency of 87.62 Hz without loss of efficacy, as is demonstrated in the following Example, Batch 18.

The following Example illustrates a representative methodology for developing and identifying candidate non-regular stimulation trains as shown in FIGS. 3 to 5 that achieve comparable or better efficacy at a lower average frequency (i.e., more efficiency) than constant inter-pulse interval trains or better efficacy at the same average frequency than constant inter-pulse interval trains.

EXAMPLE

Computational models of thalamic DBS and subthalamic DBS can be used with genetic-algorithm-based optimization (GA) to design non-regular stimulation patterns or trains that produce desired relief of symptoms with a lower average stimulation frequency than regular, high-rate stimulation and/or greater relief of symptoms.

In the GA implementation, the stimulus train (pattern) is the chromosome of the organism, and each gene in the chromosome is the IPI between two successive pulses in the train. The implementation can start, e.g., with trains of 21 pulses (20 genes) yielding a train length of ~400 ms (at average frequency of 50 Hz), and the 6 s trains required for stimulation are built by serial concatenation of 15 identical pulse trains. The process can start with an initial population of, e.g., 50 organisms, constituted of random IPI's drawn from a uniform distribution. At each step (generation) of the GA, the fitness of each pulse train is evaluated using either the TC or basal ganglia network model (identified above) and calculating a cost function, C. From each generation, the 10 best stimulus trains (lowest C) are selected, to be carried forward to the next generation. They will also be combined (mated) and random variations (mutations) introduced into the 40 offspring, yielding 50 trains in each generation. This process assures that the best stimulation trains (traits) are carried through to the next generation, while avoiding local minima (i.e., mating and mutations preserve genetic diversity). The GA continues through successive generations until the median and minimum values of the cost function reach a plateau, and this will yield candidate trains.

The objective is to find patterns of non-constant inter-pulse interval deep brain stimulation trains that provide advantageous results, as defined by low frequency and low error rate, i.e., low symptoms and/or secondarily a low average frequency. An error function is desirably created that assigns the output of each temporal pattern of stimulation a specific error fraction (E) based on how the voltage output of the thalamic cells correspond to the timing of the input stimulus. Using this error fraction, a cost function (C) is desirably created to minimize both frequency and error fraction and/or frequency, according to representative equation $C=W*E+K*f$, where C is the cost, E is the error fraction, f is the average frequency of the temporal pattern of stimulation, W is an appropriate weighting factor for the error function, and K is an appropriate weighting factor for the frequency. The weighting factors W and K allow quantitative differentiation between efficacy (E) and efficiency (f) to generate patterns of non-constant inter-pulse interval deep brain stimulation trains that provide advantageous results with superior reduction of symptoms at comparable or lower average frequencies, compared to conventional constant frequency pulse trains.

With this cost function, the voltage output of several candidate temporal patterns of stimulation can be evaluated and the cost calculated. Temporal patterns of stimulation with a low cost can then be used to create new temporal patterns of similar features in an attempt to achieve even lower costs. In this way, new temporal patterns of stimulation can be "bred" for a set number of generations and the best temporal patterns of stimulation of each batch recorded.

Several batches of the genetic algorithm yields useful results in that they achieve lower costs than the corresponding constant frequency DBS waveforms. Some batches may be run in an attempt to find especially low frequency and/or high efficacy temporal patterns of stimulation, by changing the cost function to weight frequency and/or fractional error (E) more heavily, or vice versa (i.e., by changing W and/or K). These batches can also yield lower cost results than the constant-frequency waveforms.

By way of example, a total of 14 batches of the genetic algorithm were run and evaluated with various cost functions and modified initial parameters.

Figure 6:
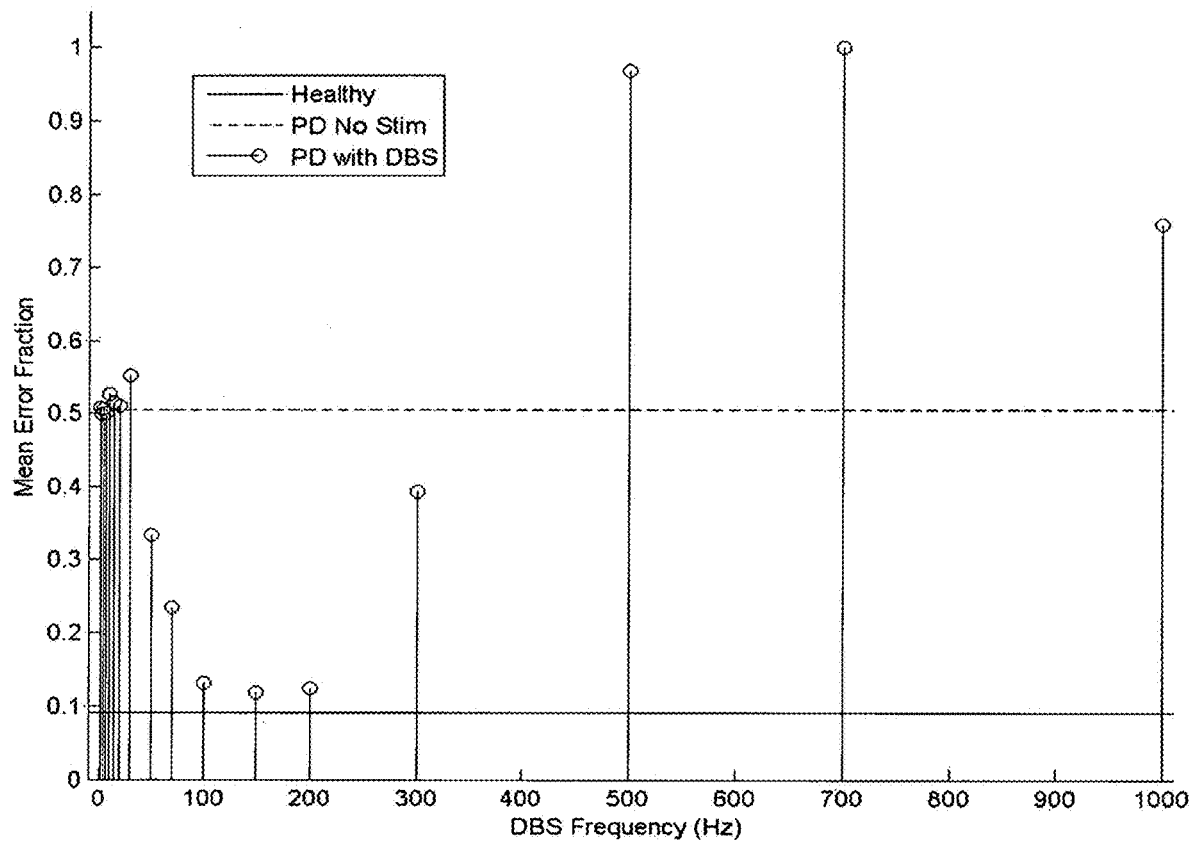
FIG. 6 is a reproduction of Example FIG. 1, as described below.

Before the trials were run, a baseline was established by running constant-frequency patterns of stimulation through the model and analyzing the associated error fractions (Example FIG. 1). As can be seen from Example FIG. 1 (FIG. 6), the healthy condition produced a low error fraction of 0.1 while the Parkinsonian condition without DBS yielded a higher error fraction of 0.5. From these results, constant high-frequency patterns of stimulation ranging from 100-200 Hz gave near perfect results. Novel non-constant temporal patterns of stimulation would then be considered advantageous if they showed error fractions very close to 0.1 with average frequencies less than 100-200 Hz.

Figure 7:
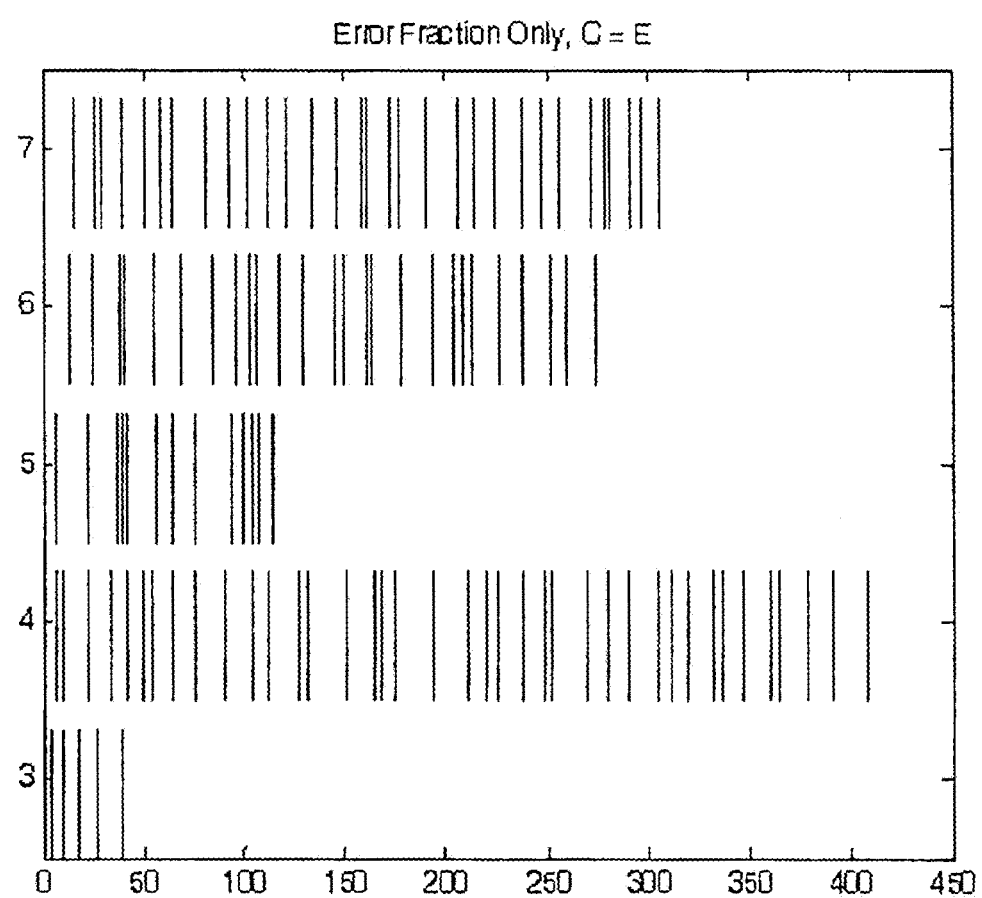
FIG. 7 is a reproduction of Example FIG. 2, as described below.
Figure 8:
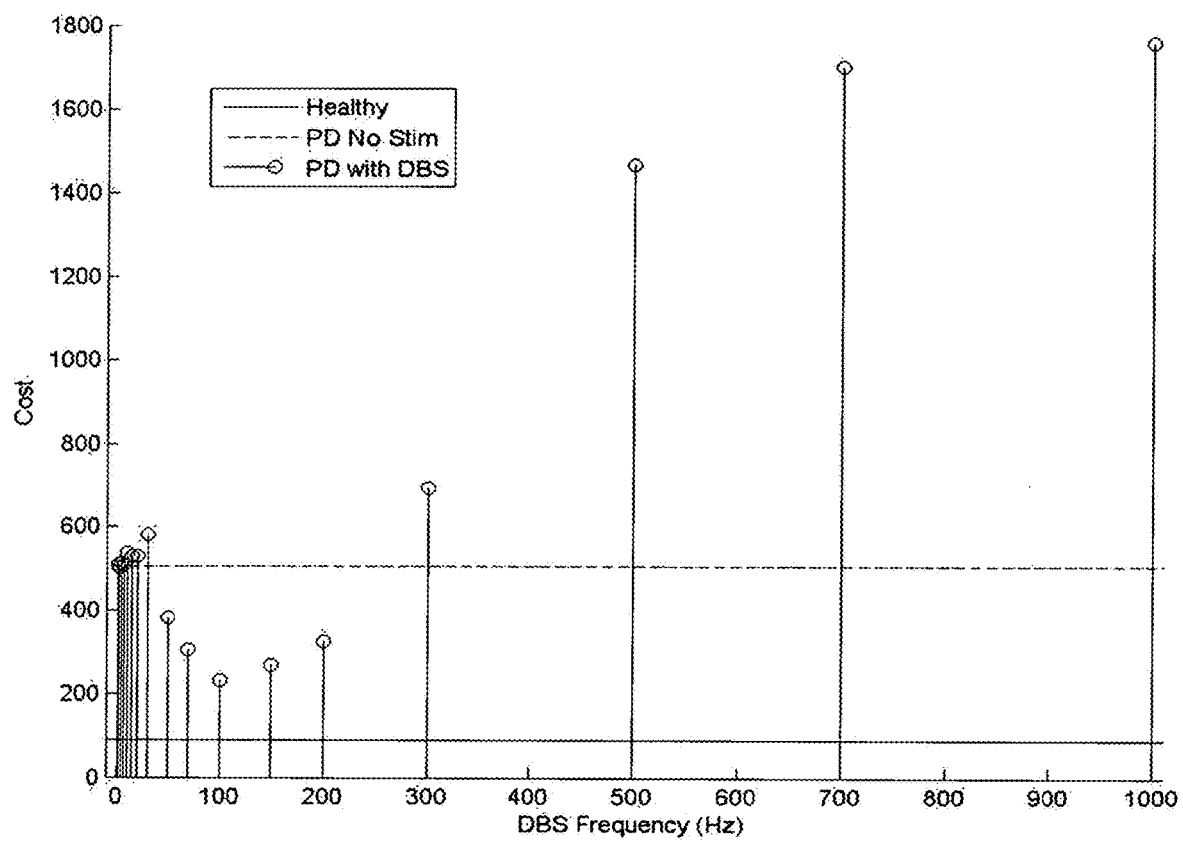
FIG. 8 is a reproduction of Example FIG. 3, as described below.

The first set of batches was run by minimizing only the error fraction (E). Thus, the associated cost function was simply C=E. The results are summarized according to average frequency and error fraction (Example Table 1). The associated inter-pulse intervals (IPI's) can be seen in Example FIG. 2 (FIG. 7). Batch 3 outputted an error fraction 0.054. Another feature is that the IPI's in Batch 3 gradually increased until about 40 msec, and then repeated itself. This provides support that ramp trains are advantageous. The trace shown in FIG. 3 generally incorporates the temporal features of Batch 3.

The remaining batches yielded error fractions higher than 0.1 and were no better than the 150 Hz constant-frequency case.

Example TABLE 1

| Error Fraction Only, C = E | | | |
|---|---|---|---|
| # | Average Frequency | Error Fraction | IPI Length |
| 3 | 127.5 | 0.054 | 5 |
| 4 | 95.62 | 0.162 | 39 |
| 5 | 113.6 | 0.139 | 13 |
| 6 | 94.64 | 0.132 | 26 |
| 7 | 101.6 | 0.142 | 31 |

Because many batches were yielding error fractions above 0.1 (healthy condition), and only a small window of error fraction less than the 150 Hz DBS case would be useful, a new cost function was constructed to minimize an alternate feature of the temporal patterns of stimulation; namely, frequency. This new cost function weighted the error fraction and frequency, yielding the equation $C=1000*E+F$, where C is cost, E is error fraction, and F is the average frequency of the waveform in Hz, W=1000, and K=1.

In order to establish a new baseline cost, the constant-frequency patterns of stimulation were evaluated again according to the new cost function (Example FIG. 3-FIG. 8). As can be seen from the graph, the healthy condition reported a cost of 90.65 and the Parkinson case with no DBS yielded 505.50. The best constant-frequency pattern of stimulation with the new cost function was the 100 Hz case with a cost of 231.11. This new cost function allowed for a wider range of solutions, because a temporal pattern of stimulation would be considered useful if it had a cost less than 231.11 but presumably higher than 90.65.

Figure 9:
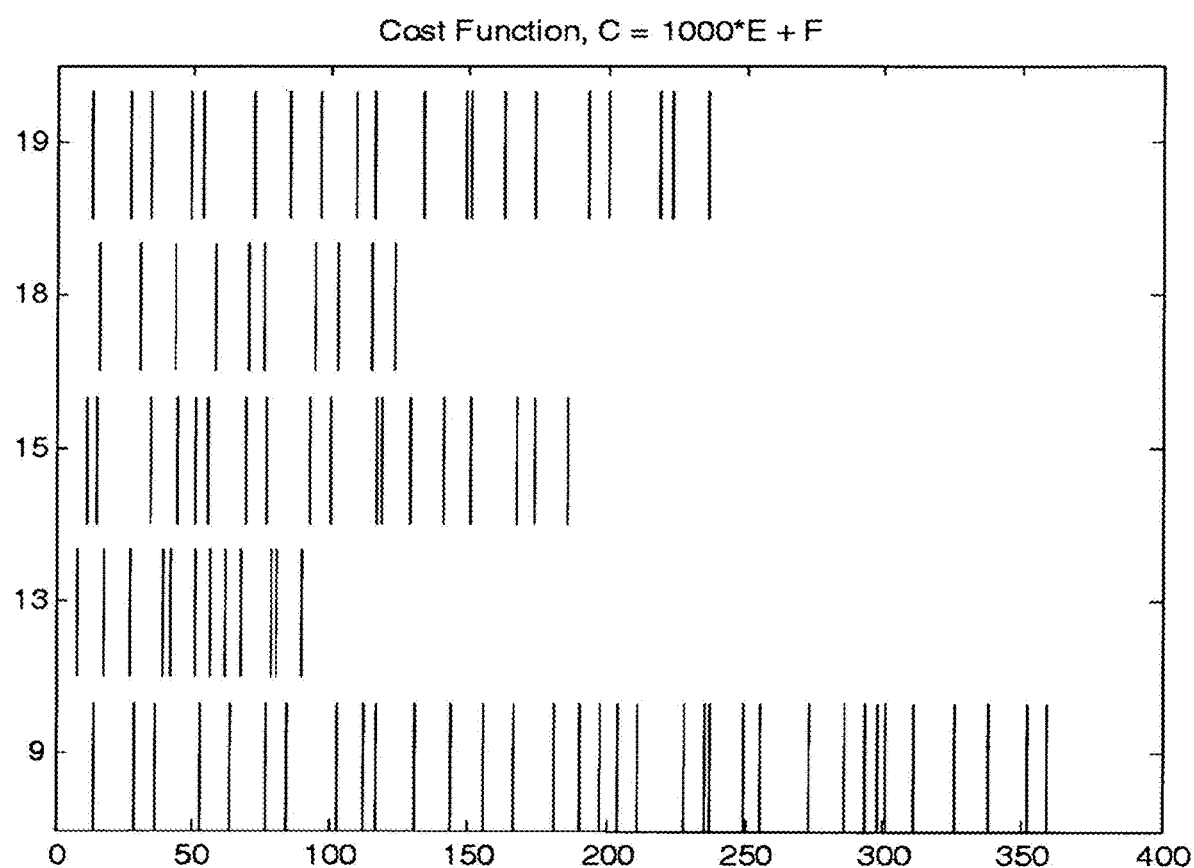
FIG. 9 is a reproduction of Example FIG. 4, as described below.

The results of the new cost function can be seen in Example Table 2 and the IPI's visualized in Example FIG. 4 (FIG. 9). The best results were seen in batches 15 and 18, which had the lowest costs. Batch 18 also exhibits a ramp-like pattern of increasing interpulse intervals. It shows a steadily falling IPI, followed by a sudden rise, and then a quick fall, rise, and fall—almost as if it consists of 3 smaller ramps. The trace shown in FIG. 5 generally incorporates the temporal features of Batch 18. Batch 15 also performed very well, but its qualitative features are more difficult to discern.

Example TABLE 2

| Cost Function, C = 1000*E + F | | | |
|---|---|---|---|
| # | Average Frequency | IPI Length | Error Fraction | Cost |
| 9 | 94.74 | 34 | 0.124 | 218.8 |
| 13 | 132.9 | 12 | 0.087 | 219.4 |
| 15 | 98.00 | 17 | 0.098 | 196.0 |
| 18 | 81.28 | 10 | 0.116 | 197.3 |
| 19 | 84.70 | 20 | 0.116 | 201.2 |

The advantage of low frequency was emphasized with a new cost function, which weighted frequency more heavily, $C=1000*E+2*F$. Because the frequency of DBS does not affect the healthy condition or the PD with no DBS, these baseline costs stayed the same at 90.65 and 505.50, respectively. The 100 Hz was again the best constant-frequency temporal pattern of stimulation, with a cost of 331.11. The following temporal patterns of stimulation, then, were considered useful if they had low frequencies and costs less than 331.11 and greater than 90.65.

Figure 10:
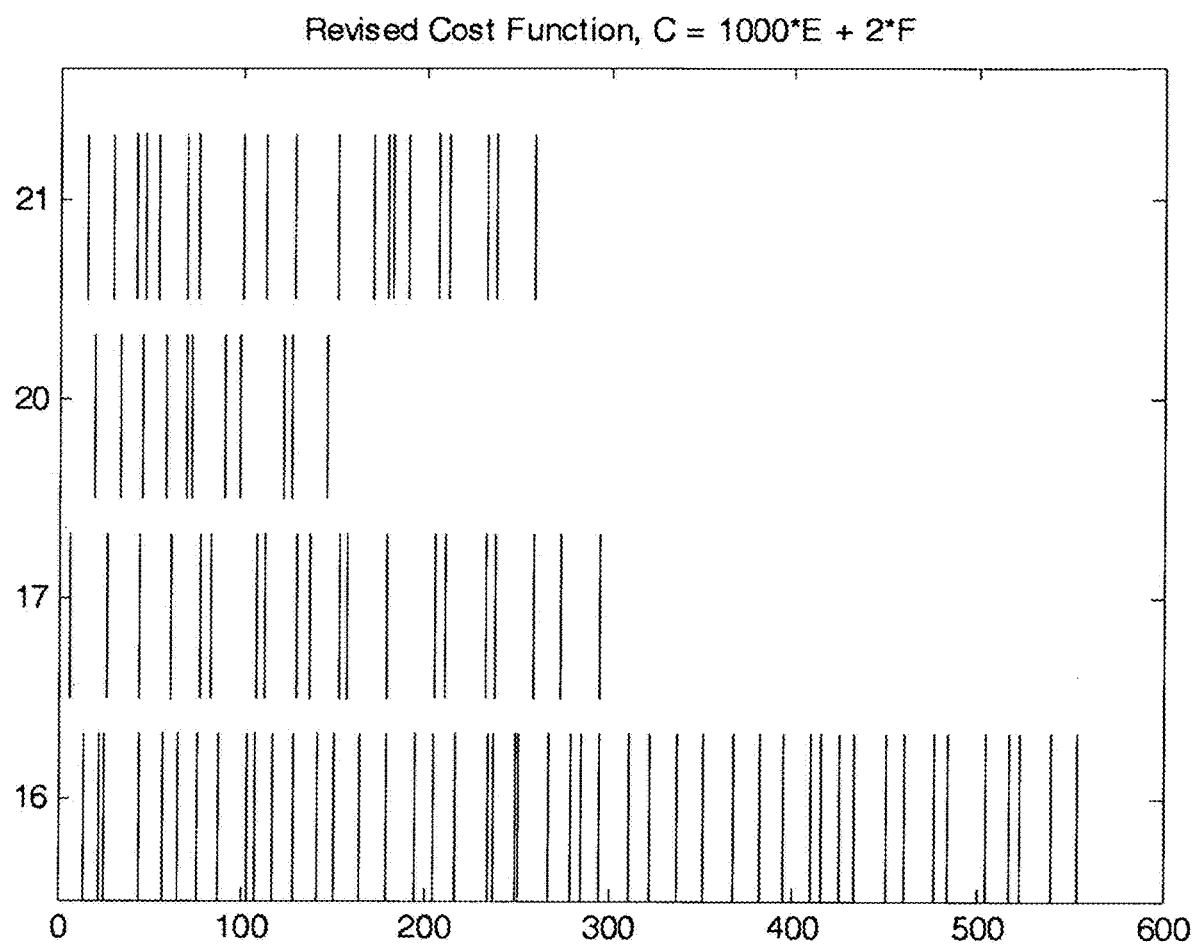
FIG. 10 is a reproduction of Example FIG. 5, as described below.

The results of the revised cost function can be seen in Example Table 3 and the IPI's visualized in Example FIG. 5 (FIG. 10). Of the resulting batches, batch 17 proved most interesting because of its very low average frequency of 67.82 Hz. Even with such a low frequency, it managed to prove better than the 100 Hz condition with a reduction in cost of about 10. The waveform of batch 17 is interesting in that it consists of a ramp pattern of decreasing IPI in the first 100 msec, followed by a continual shift between large IPI and small IPI. The qualitative feature of quickly changing between large and small IPI's may prove advantageous. The trace shown in FIG. 4 generally incorporates the temporal features of Batch 17.

Example TABLE 3

| Revised Cost Function, Cost = 1000*E + 2*F | | | |
|---|---|---|---|
| # | Average Frequency | IPI Length | Error Fraction | Cost |
| 16 | 84.92 | 47 | 0.239 | 323.8 |
| 17 | 67.82 | 20 | 0.253 | 321.1 |
| 20 | 79.25 | 10 | 0.236 | 315.4 |
| 21 | 77.15 | 20 | 0.269 | 346.6 |

The most interesting temporal patterns of stimulation in this Example are from batches 15, 17, and 18. Batch 15 produced a temporal pattern of stimulation with an average frequency of 98 Hz with an error fraction as low as 0.098. Thus, it outperformed the 100 Hz constant-frequency case by managing to lower the error even further at roughly the same frequency. Still, the qualitatively useful features of batch 15 are difficult to discern. Batch 17 was also appealing because of its very low frequency of 67.82. This low frequency was gained at the cost of increased error at 0.253, but it may nonetheless be useful if emphasis is placed on maintaining low frequency DBS. The qualitative features of batch 17 indicated at first a ramp followed by a continual switching between low and high IPI's. Lastly, batch 18 stood somewhere in the middle with a fairly low frequency of 87.62 and low error fraction of 0.116, only marginally higher than the healthy condition of 0.1. The dominant qualitative feature of batch 18's waveform is that it too shows a ramp nature in that the IPI initially steadily falls, then quickly rises, falls, and then rises. The rapid changing between high and low IPI of batch 17 can be envisioned as a set of steep ramps.

A comparison of Batch 17 (FIG. 4) and Batch 18 (FIG. 5) demonstrates how the balance between efficacy (as a function of the model error fraction E) and efficiency (as a function of frequency f) in non-regular temporal patterns of stimulation can be purposefully tailored to meet clinical objectives. The systems and methodologies discussed allow changing the cost function by weighting efficacy or frequency more heavily (i.e., by changing W and/or K), while still yielding temporal patterns of stimulation with lower cost results than the constant-frequency waveforms. Comparing Batch 17 with Batch 18, one sees that the error fraction (E) (i.e., the efficacy of the temporal pattern) of Batch 17 (0.253) is greater than the error fraction (E) (i.e., the efficacy of the temporal pattern) of Batch 18 (0.116). However, one can also see that the efficiency (i.e., the average frequency) of Batch 17 (67.82 Hz) is lower than the efficiency (i.e., the average frequency) of Batch 18 (81.28 Hz). Through different in terms of efficacy and efficiency, both Batch 17 and Batch 18 have costs better than constant-frequency temporal patterns.

Figure 11:
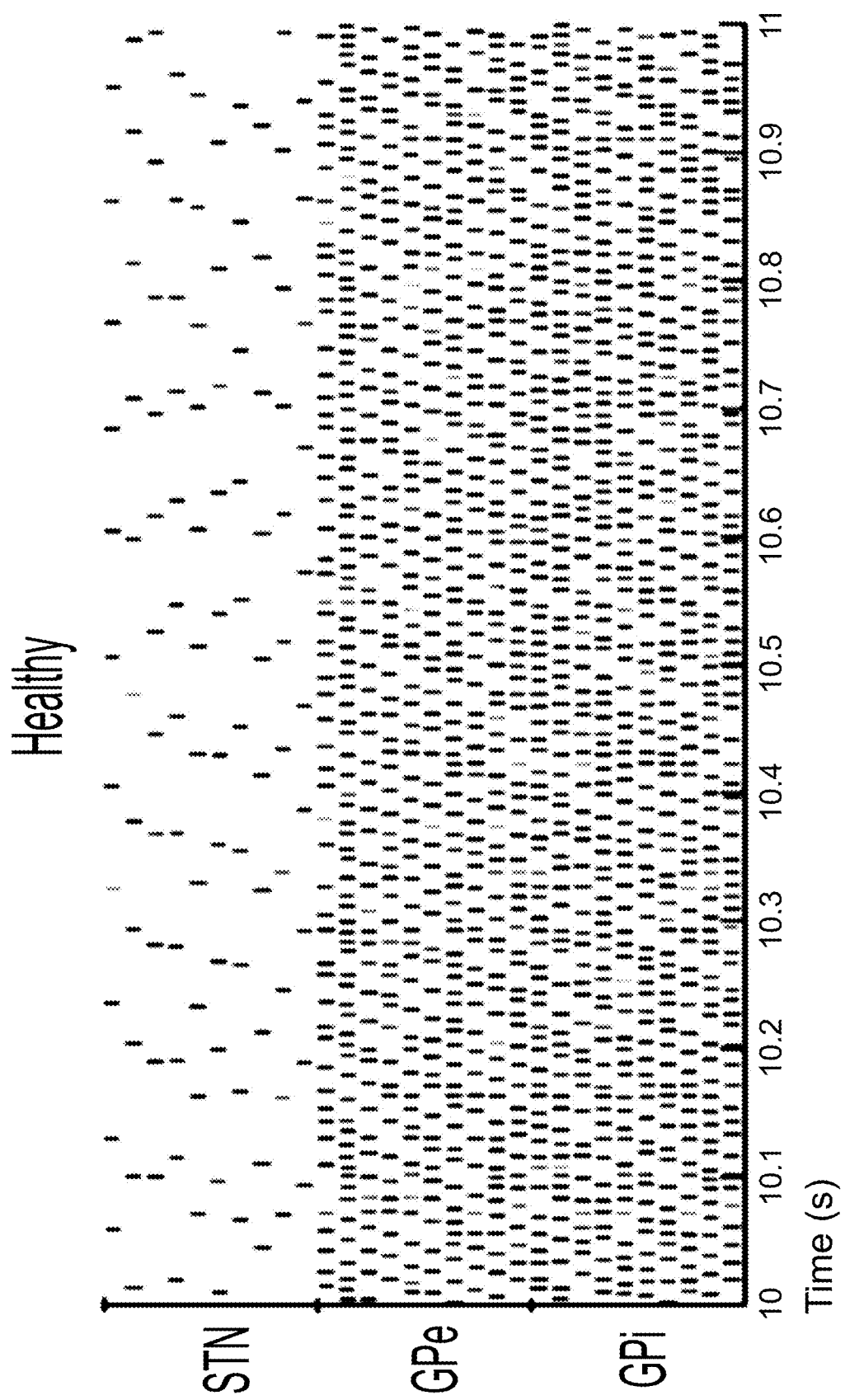
FIG. 11 is a raster of the neuronal firings of ten neurons in each of the subthalamic nucleus, the global pallidus exterior, and the global pallidus interior, generated by a computer model of a healthy human.

FIG. 11 depicts a modeled raster of healthy firing of neurons in the subthalamic nucleus and the global pallidus, both external and internal segments thereof, through about one second of time.

Figure 12:
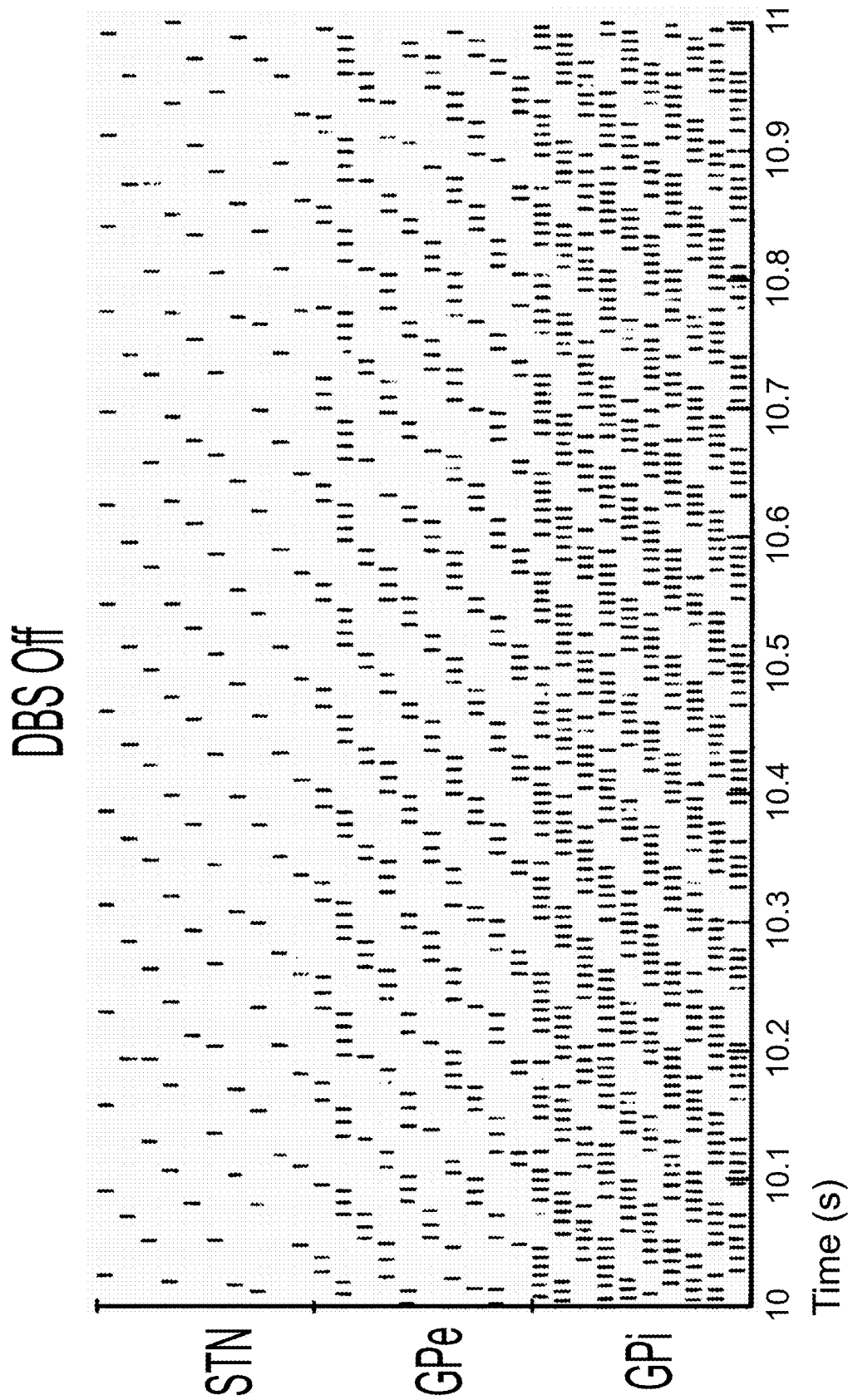
FIG. 12 is a raster of the neuronal firings of ten neurons in each of the subthalamic nucleus, the global pallidus exterior, and the global pallidus interior, generated by a computer model of a human having a neurological condition, such as PD.

FIG. 12 depicts a modeled raster of the healthy subject modeled in FIG. 11, with the addition of a forced Parkinsonian state, however with deep brain stimulation not being applied to the model. Like the raster of FIG. 11, this Figure depicts neurons in the subthalamic nucleus and the global pallidus, both external and internal segments thereof, through about one second of time.

Figure 13:
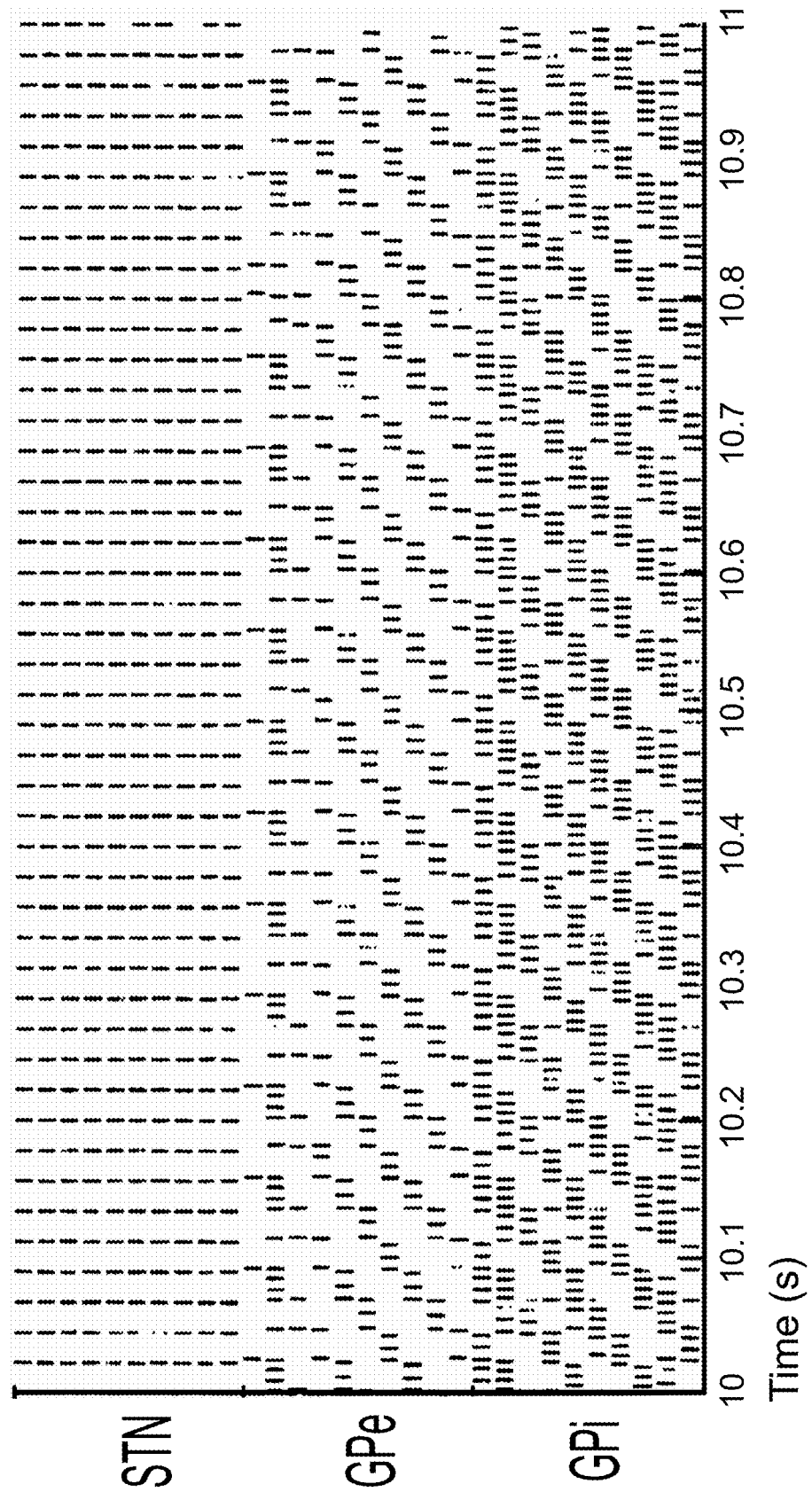
FIG. 13 is a raster of the neuronal firings of ten neurons in each of the subthalamic nucleus, the global pallidus exterior, and the global pallidus interior, generated by a computer model of an electrical deep brain stimulation of regular interval applied to the subthalamic nucleus at 45 Hertz.

FIG. 13 depicts a modeled raster of the modeled Parkinsonian subject of FIG. 12, however further applying a regular 45 Hz regular interval DBS signal to the subthalamic nucleus, as can be seen. Additionally, the figure shows the firing of neurons in the global pallidus, both external and internal segments thereof, through about one second of time.

Figure 14:
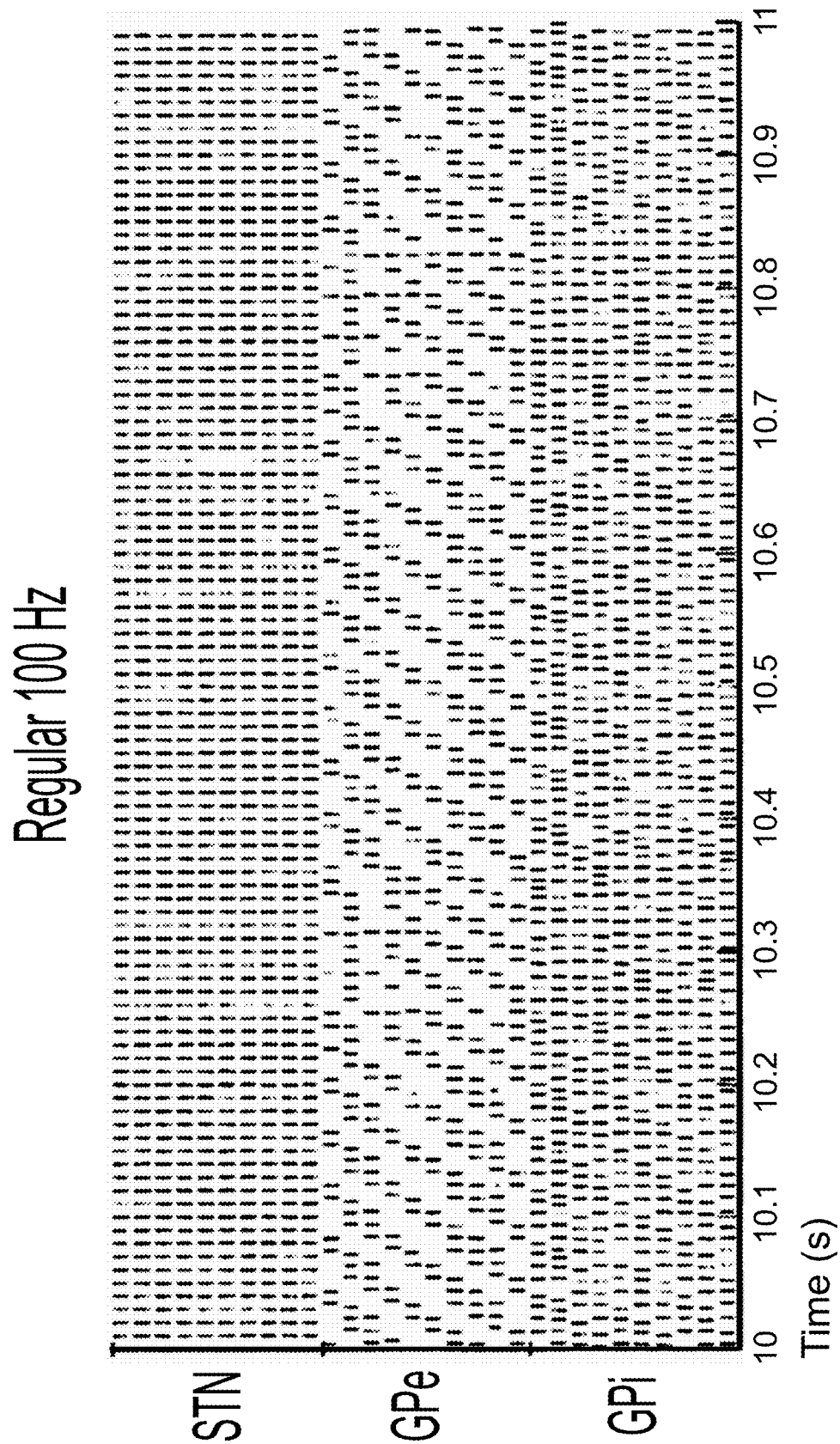
FIG. 14 is a raster of the neuronal firings of ten neurons in each of the subthalamic nucleus, the global pallidus exterior, and the global pallidus interior, generated by a computer model of an electrical deep brain stimulation of regular interval applied to the subthalamic nucleus at 100 Hertz.

FIG. 14 depicts a modeled raster of the modeled Parkinsonian subject of FIG. 12, however further applying a regular 100 Hz regular interval DBS signal to the subthalamic nucleus, as can be seen. Additionally, the figure shows the firing of neurons in the global pallidus, both external and internal segments thereof, through about one second of time.

Figure 15:
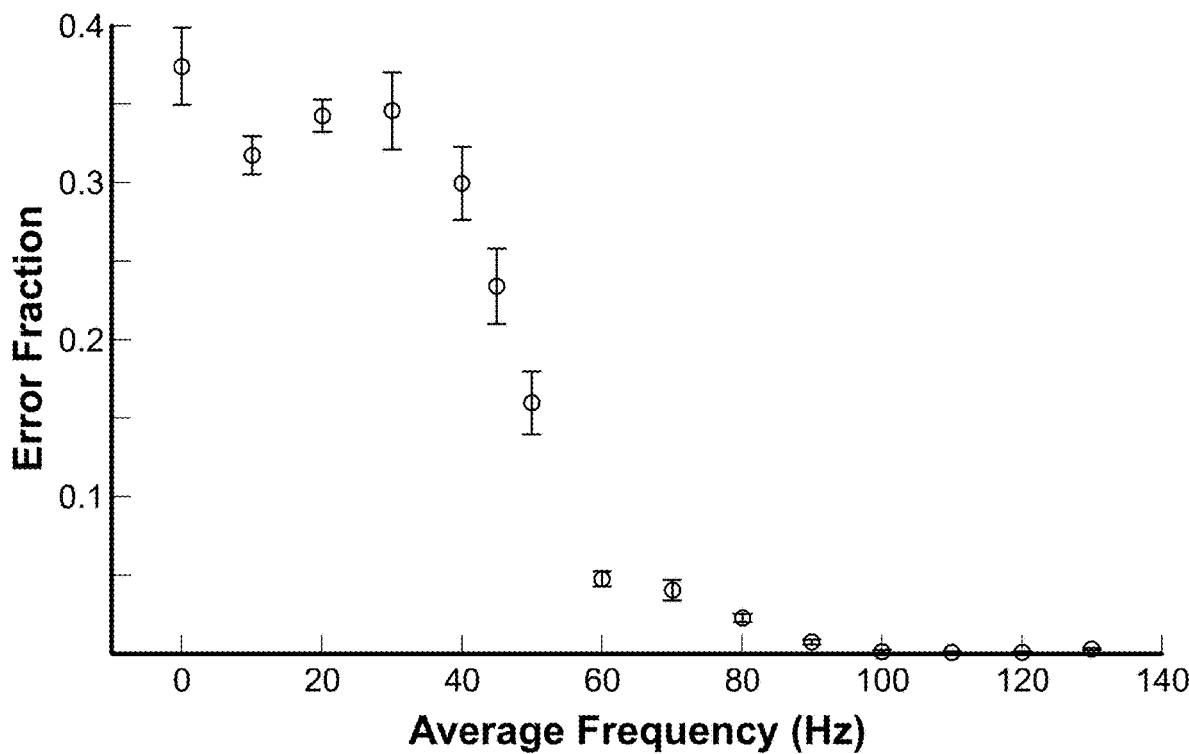
FIG. 15 is a plot of a computer-generated error fraction of a regular interval electrical DBS applied at the given average frequency.

FIG. 15 depicts a graphical representation of modeled, conventionally expected error fractions where a regular interval DBS signal is applied to the Parkinsonian model. The goal in determining optimum stimulation patterns may be to provide a stimulation pattern that has a lower average frequency with at least as good, if not better (lower) error fractions than regular interval DBS signals presented to the STN. By way of a non-limiting example, with DBS off (average frequency=0 Hz), the model provides that an expected error fraction may be about 0.34 to about 0.40. With a regular interval stimulation pattern applied to the STN at about 45 Hz, the expected error fraction is about 0.20 to about 0.25. According to the model, and therefore generally accepted in the field, higher average frequency regular interval stimulation yields a lower error fraction. Accordingly, if stimulation could be provided at an average frequency of about 45 Hz with a modeled error fraction less than that expected (i.e., less than about 0.20), benefits would be realized. Not only would relief from brain disorders be improved, but power consumption by any device delivering the new stimulation patterns, would be reduced as compared to the same device delivering regular interval stimulation patterns in an attempt to achieve similar performance results.

Figure 16:
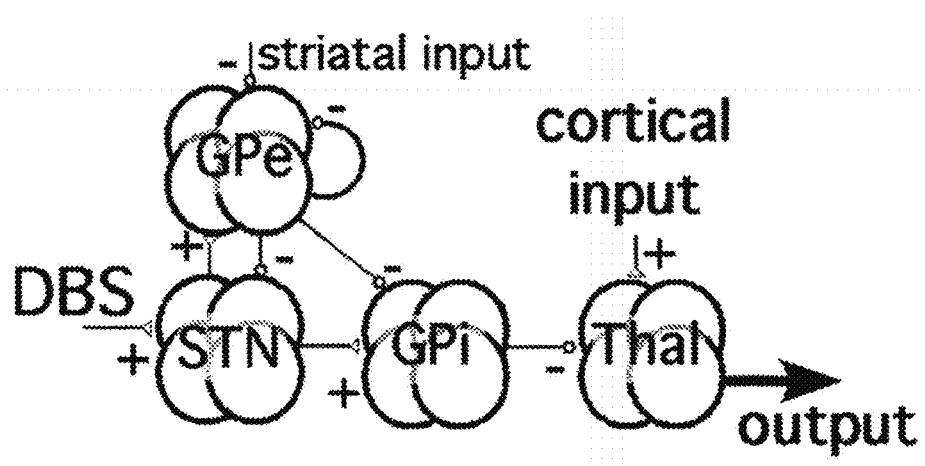
FIG. 16 diagrammatically illustrates an embodiment of a computer model that may be used to analyze and generate stimulation patterns according to the present invention.

FIG. 16 provides an illustration of a model structure that may be used to generate stimulation patterns according to the present invention. Reference to this illustration may be helpful in explaining what is referred to herein as an "error fraction." As used herein, an "error fraction" is generally understood to mean the number of errors occurring at the output of a model as compared to the number of inputs provided to the model. An output error occurs when a contrast arises between an expected value of the model output to an output generated by the model provided with a given stimulation pattern, such as to the STN, as shown.

Figure 17:
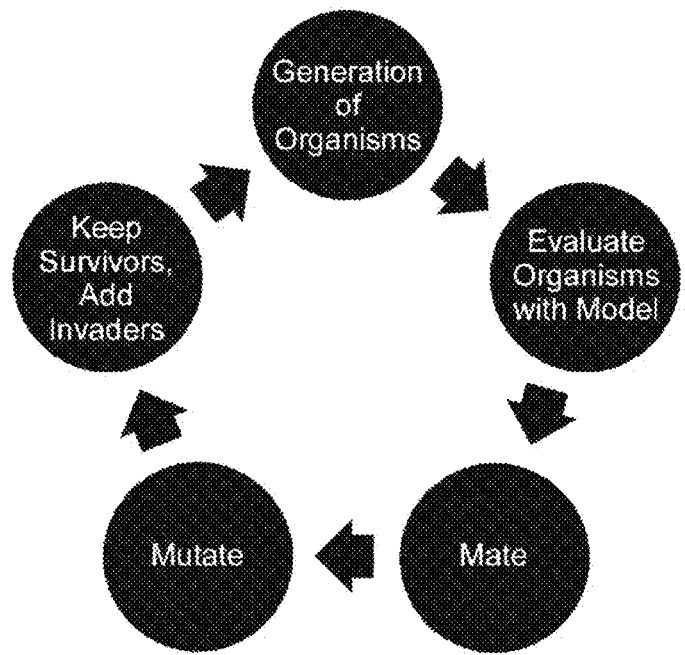
FIG. 17 is a diagram of a general genetic algorithm process.
Figure 18:
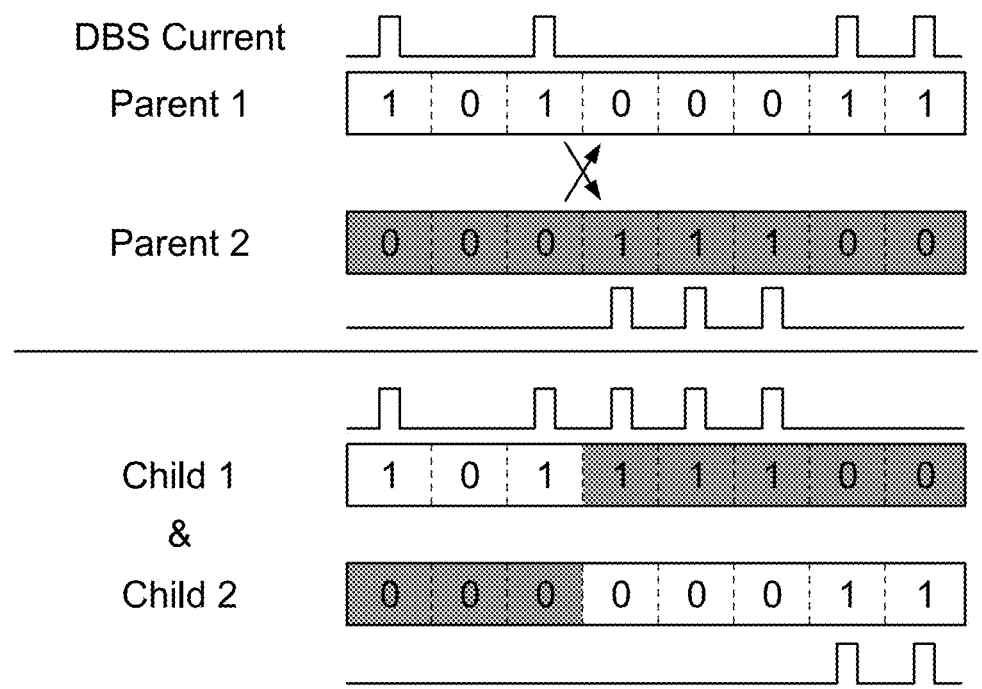
FIG. 18 is an embodiment of a generational crossover of stimulation patterns according to the present invention.

FIG. 17 generally depicts a known genetic algorithm process model, beginning with the generation of organisms (in this case pulse trains or stimulation patterns), and continuing as described above. One method for a mating process that may be employed in the genetic algorithm according to the present invention is a single crossover process by which certain, but preferably not all, genes (stimulation pulses) are exchanged between parent stimulation trains so as to yield two child stimulation trains are generated. As depicted in FIG. 18, the stimulation patterns include a series of 1's and 0's, which indicate whether or not, respectively, a stimulation pulse is to be delivered during a given time step, such as about 500 microseconds to about 100 milliseconds, and preferably about one to 5 milliseconds. While initial or starting stimulation patterns may be created by drawing interpulse intervals from some distribution, such as a Gaussian distribution, the initial stimulation patterns are preferably generated randomly, and constraints may be added to control the number of stimulation pulses (1's) in the initial stimulation patterns, thereby controlling the average frequency range of the stimulation pattern. Resulting generational stimulation patterns are then evaluated by the model and compared to the performance of regular interval stimulation patterns provided to the model at the same average frequency as the generational stimulation pattern currently under evaluation.

Figure 19:
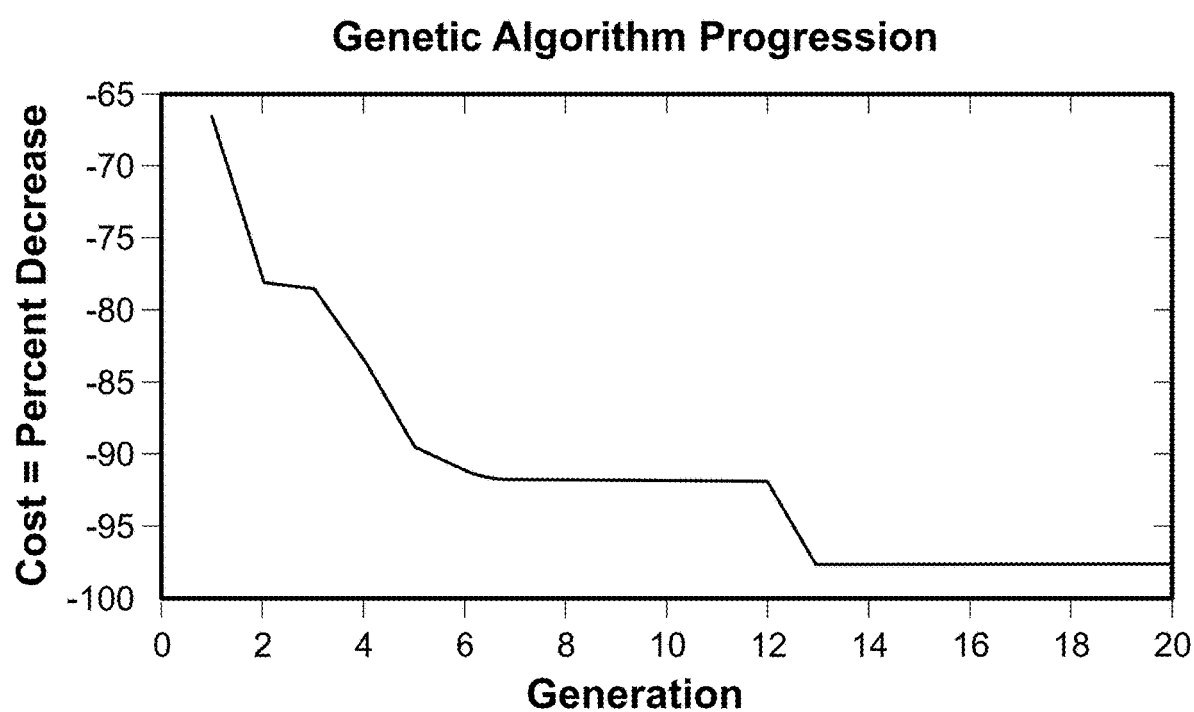
FIG. 19 is a plot of a percent decrease cost function versus the number of generations run in an evolutionary algorithm according to the present invention.

Another cost function that has proven useful in determining beneficial non-regular temporal patterns of stimulation generated by a genetic algorithm is as follows: $C=(E_{GA}-E_{FMReg})/E_{FMReg}*100\%$ where $E_{GA}$ is the error fraction of a selected generational stimulation pattern generated by the genetic algorithm and currently under analysis by the model and $E_{FMReg}$ is the error fraction of a DBS stimulation pattern of uniform frequency at a frequency equal to the average frequency of the GA train under analysis. This may be referred to generally as a percent change cost function. At first, one might expect that this cost function would not force a genetic algorithm to search for non-regular patterns of DBS with a low average frequency. However, this is not the case; the GA is inclined to search for non-regular stimulation pattern of DBS with a low average frequency because there is a greater opportunity to find improved stimulation patterns (i.e., having a lower error fraction) at lower frequencies. That is, as shown in FIG. 15, the error fraction associated with 130 Hz conventional regular-interval DBS is already so close to zero that it is highly unlikely that a non-regular pattern with an average frequency of 130 Hz is going to have a smaller error fraction. In other words, there just is not much room to improve at 130 Hz. On the other hand, at 45 Hz, there is ample room for improvement. It is much more likely that a non-regular pattern of DBS with an average frequency of 45 Hz will be found that has a better performance than conventional regular-interval DBS provided at 45 Hz. Therefore, using a percent decrease cost function implicitly incorporates the average frequency of DBS while helping to minimize complications of selecting weighting parameters, as with the other cost functions discussed herein. As shown in FIG. 19, it is beneficial to run the genetic algorithm through a plurality of generations so as to decrease the cost. This figure shows the (decline in) cost as the genetic algorithm progresses. That is, the algorithm is identifying better and better stimulation patterns, from generation to generation, and subsequently the cost is declining, or, in other words, the performance is increasing.

Figure 20:
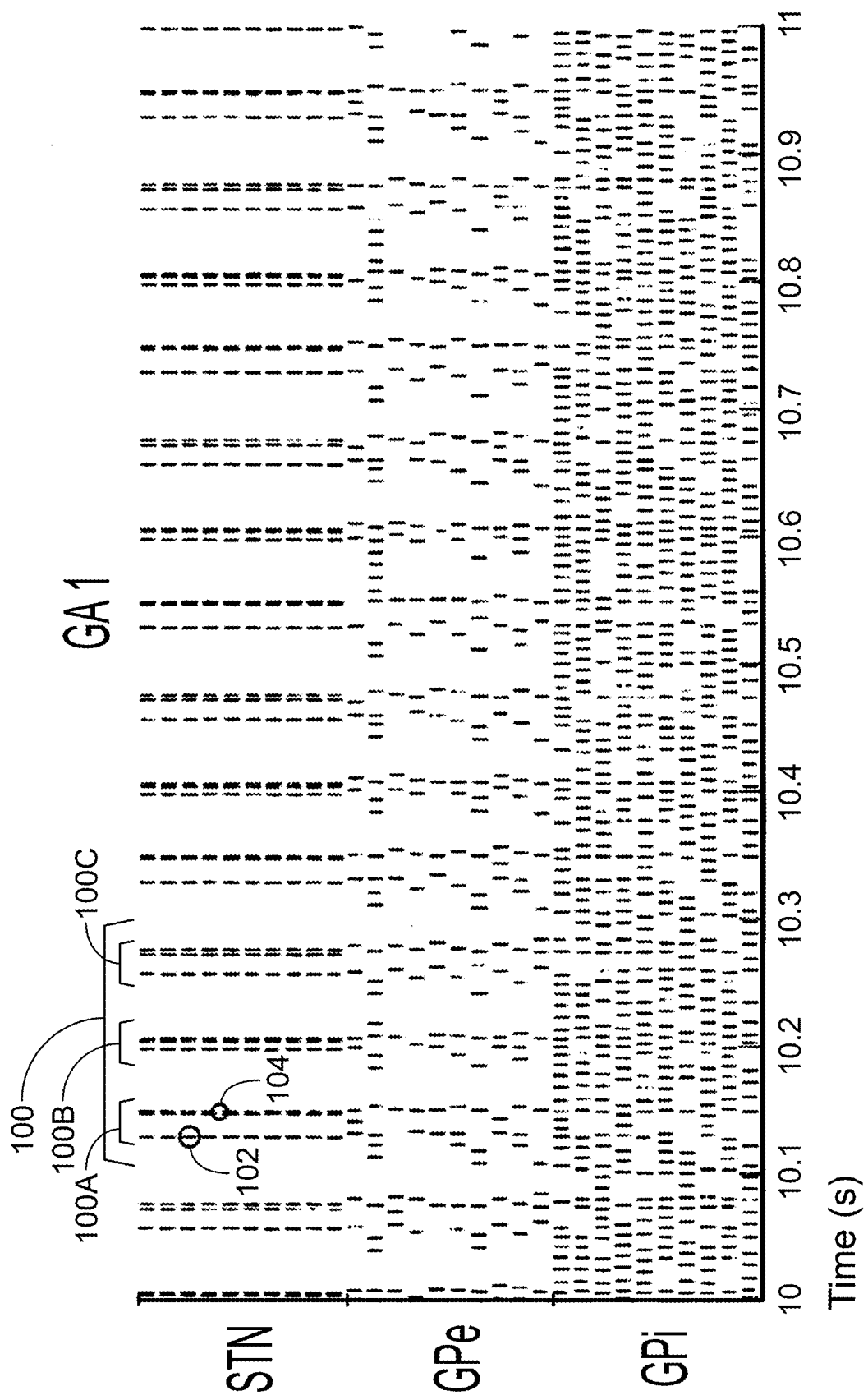
FIG. 20 is a raster of the neuronal firings of ten neurons in each of the subthalamic nucleus, the global pallidus exterior, and the global pallidus interior, generated by a computer model of an electrical deep brain stimulation applied to the subthalamic nucleus according to a first embodiment of a stimulation pattern according to the present invention.
Figure 21:
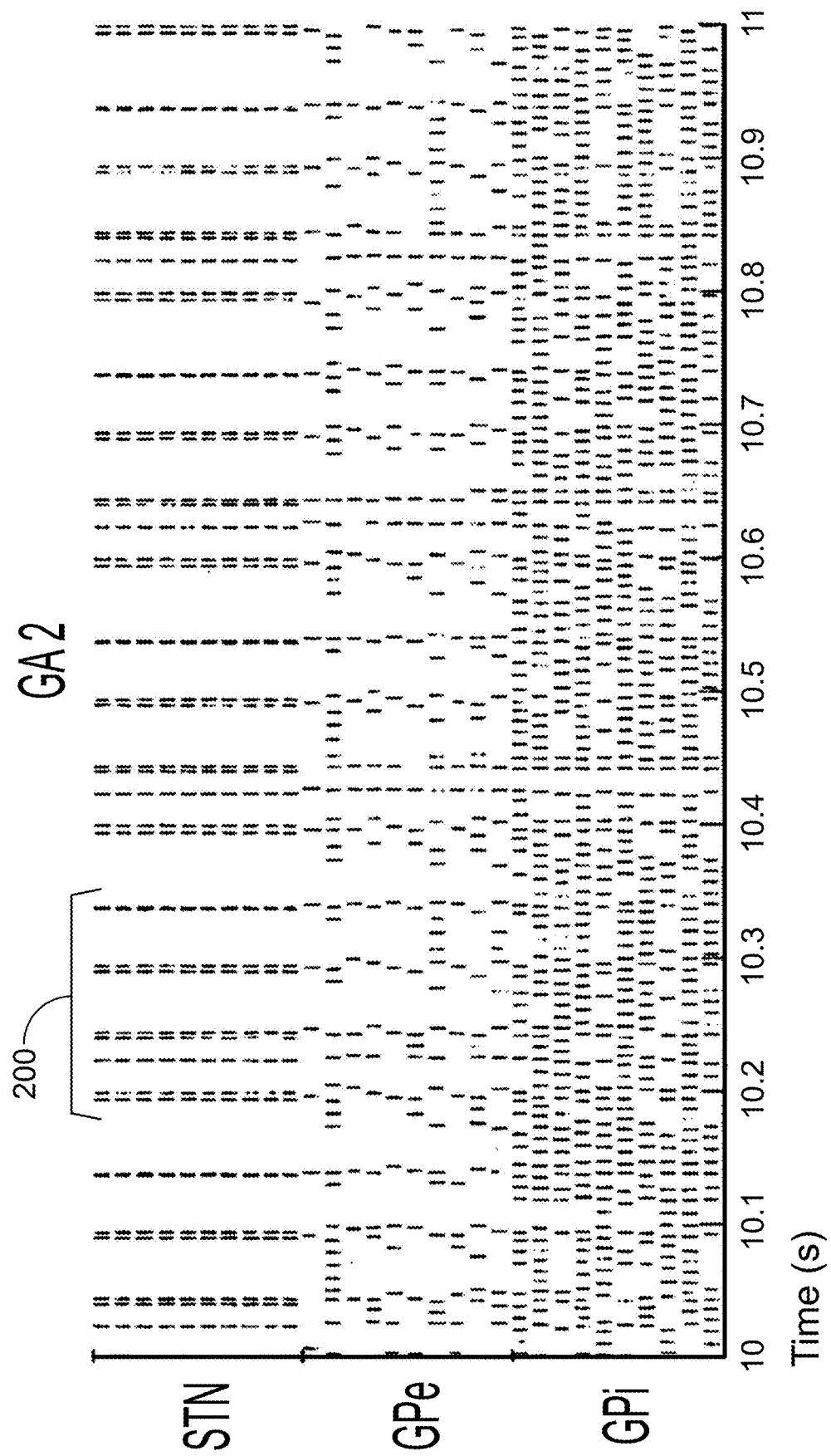
FIG. 21 is a raster of the neuronal firings of ten neurons in each of the subthalamic nucleus, the global pallidus exterior, and the global pallidus interior, generated by a computer model of an electrical deep brain stimulation applied to the subthalamic nucleus according to a second embodiment of a stimulation pattern according to the present invention.
Figure 22:
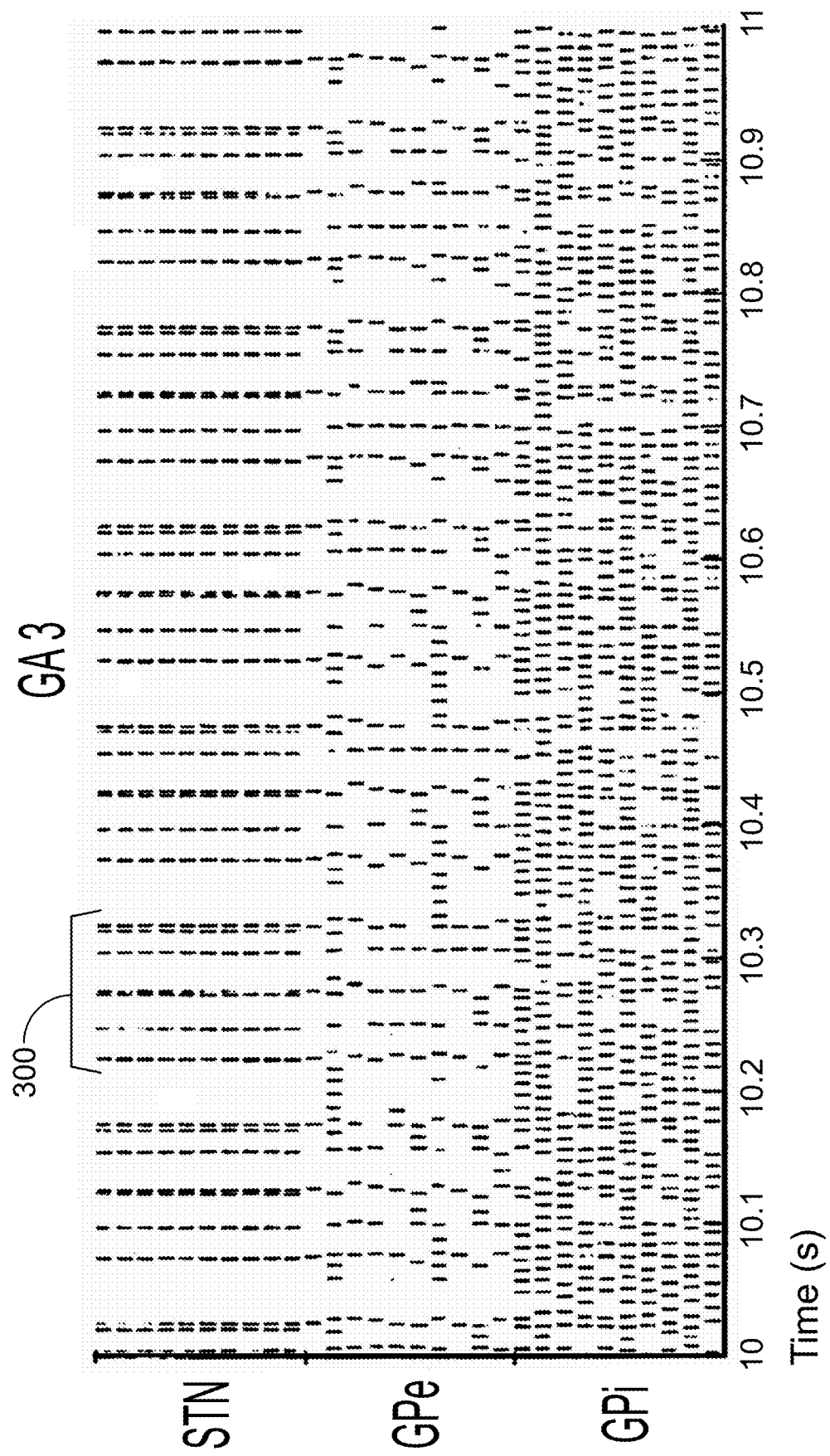
FIG. 22 is a raster of the neuronal firings of ten neurons in each of the subthalamic nucleus, the global pallidus exterior, and the global pallidus interior, generated by a computer model of an electrical deep brain stimulation applied to the subthalamic nucleus according to a third embodiment of a stimulation pattern according to the present invention.

Three stimulation trains generated according to the present invention utilizing the percent change cost function to guide survival and propagation are shown in FIGS. 20-22. In FIG. 20, a preferred GA1 stimulation train is shown as being applied to the STN of a Parkinsonion brain model. The preferred stimulation pattern includes the repetition of a set 100 of three triplet stimulation pulses 100A, 100B, 100C, where each triplet preferably comprises a singlet 102 followed by a doublet 104. Through any given set 100 of triplets, the interpulse interval between the singlet and doublet of one triplet is preferably different than the interpulse interval between the singlet and doublet of at least one other triplet, and more preferably different than each interpulse interval between the singlet and doublet of all other triplets in the set 100. Furthermore, the interpulse interval within the doublets of each triplet is preferably different than at least one other doublet interpulse interval within that set 100, and more preferably the interpulse interval within each doublet in a given set 100 is different than the interpulse interval within each other doublet in that set 100. While the interpulse intervals between the singlets and doublets of a given set, and within the doublets of the given set, may vary (as much as by integer factors), the interpulse interval between each triplet within a given set preferably remains relatively constant, such as by varying less than about 10% throughout the set.

In each of the described preferred stimulation patterns, a given set to be repeated includes at least one doublet and at least one singlet. As in the case of the GA1 train, the number of singlets and doublets in a given set 100 was equal (three of each). As in the case of the GA2 pattern set 200, as shown in FIG. 21, the number of doublets far outweighed the number of singlets (80% of n-lets were doublets as opposed to 20% as singlets). As in the case of the GA3 pattern set 300, as shown in FIG. 22, the number of doublets outweighed the number of singlets (60% of n-lets were doublets as opposed to 40% as singlets). Accordingly, it may be more preferable to include, in a given stimulation pattern to be repeatedly delivered to the subthalamic nucleus or other portion of the brain, one or more singlets and one or more doublets, where the number of doublets is equal to or greater than the number of singlets in the set.

Figure 23:
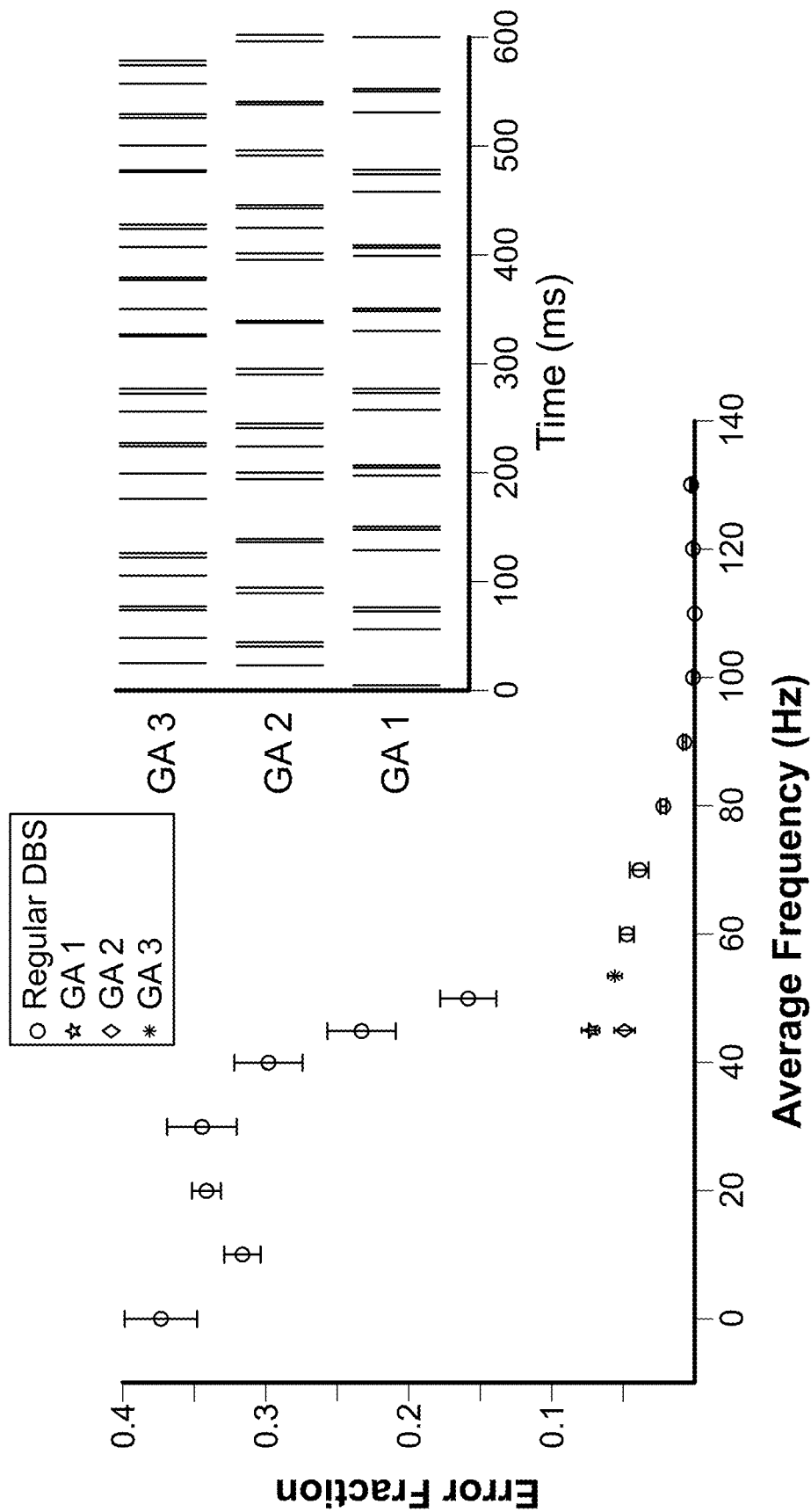
FIG. 23 is FIG. 15, further including a plot of the computer modeled error fractions generated by the use of the stimulation patterns of FIGS. 20-22.

As shown in FIG. 23, the stimulation patterns generated according to the present invention have a much lower error fraction value as compared to their regular interval stimulation counterparts at frequencies less than 100 Hz. For example, at 45 Hz, regular interval DBS has an error fraction of about 20 in 100 (0.20) to about 25 in 100 (0.25). On the other hand, the stimulation patterns generated according to the present invention provide a modeled error fraction of about 5 in 100 to about 15 in 100, thereby demonstrating a 25% to 80% improvement in efficiency.

Figure 24:
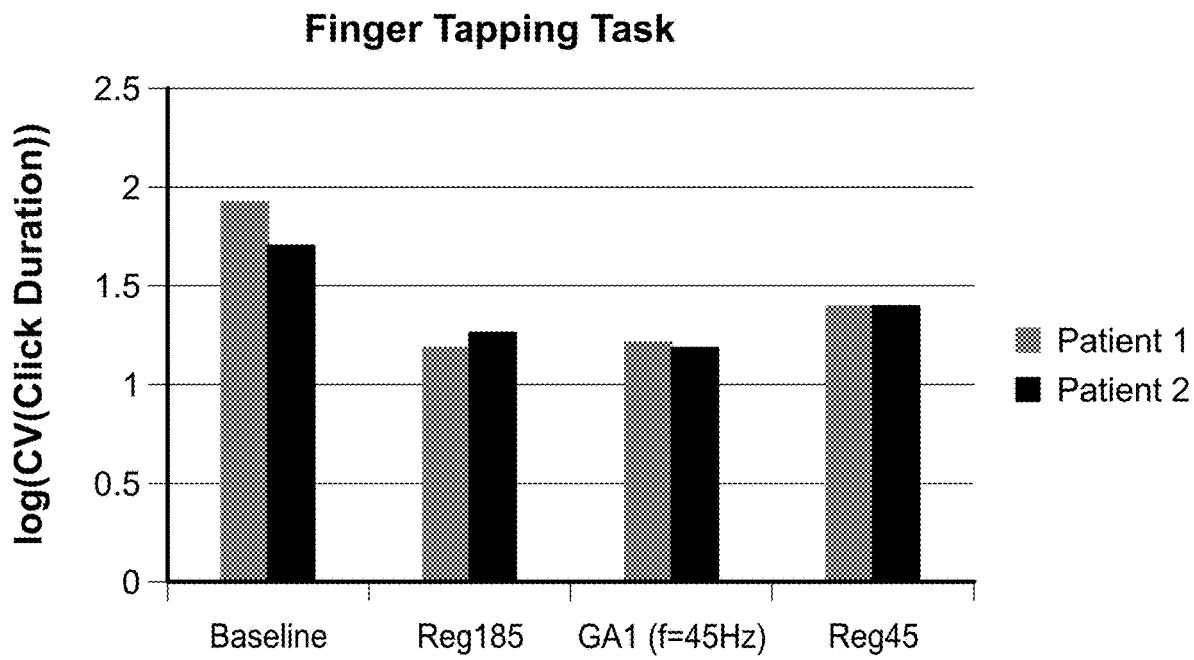
FIG. 24 is a graph of a quantitative measurement of the performance of the stimulation pattern of FIG. 20 as compared to other stimulation patterns in two human patients which had been diagnosed with PD.

An electrical stimulation pattern created according to the present invention (GA1) was experimentally applied to two human patients that had been diagnosed with PD. The GA1 pattern was applied during intraoperative experiments that were conducted by connecting to an exposed lead of a previously implanted DBS electrode during an implantable pulse generator replacement surgery. After connection, the GA1 pattern of stimulation and a few control patterns were delivered. Motor impairment was quantified while delivering the patterns of stimulation using a known finger-tapping task. To measure the effect of the DBS stimulation patterns according to the present invention, a two-button computer mouse was utilized, and the patient was instructed to, during data collection times, alternate clicking a respective mouse button with their index finger and their middle finger. The time duration of the respective button clicks was then recorded by a computer and analyzed. The time duration of one or both fingers may be analyzed, depending upon statistical results. As can be seen in FIG. 24, the GA1 stimulation pattern allowed each patient to demonstrate an increase in motor function as compared to the regular interval DBS stimulation pattern provided at the same average frequency, thus indicating an increased benefit in performance with no sacrifice to average cost (i.e., no increase in average power). Furthermore, for Patient 1, the GA1 stimulation pattern caused the patient to perform substantially similar to motor function demonstrated under application of a regular interval DBS stimulation pattern of 185 Hz, thus indicating substantial similar performance with a great cost (i.e. power) reduction (stimulation provided at an average of 45 Hz instead of 185 Hz). Finally, with respect to Patient 2, the GA1 stimulation pattern caused the patient to perform better than the motor function demonstrated under application of a regular interval DBS stimulation pattern of 185 Hz, thus indicating improved performance with a great cost (i.e. power) reduction (stimulation provided at an average of 45 Hz instead of 185 Hz). Generally speaking, then, the 45 Hz average frequency stimulation pattern designed according to the present invention performed similarly or better than conventional 185 Hz regular DBS stimulation and better than frequency matched (45 Hz) regular stimulation. Further clinical experiments have been conducted in applying stimulation to the STN using stimulation patterns generated according to the present invention, and such experiments show promising results.

An electrical stimulation pattern created according to the present invention (GA1) was also tested in one human subject with PD where tremor was that subject's primary motor symptom. The subject's tremor was quantified using as accelerometer on the back of the subject's contralateral wrist.

Figure 28A:
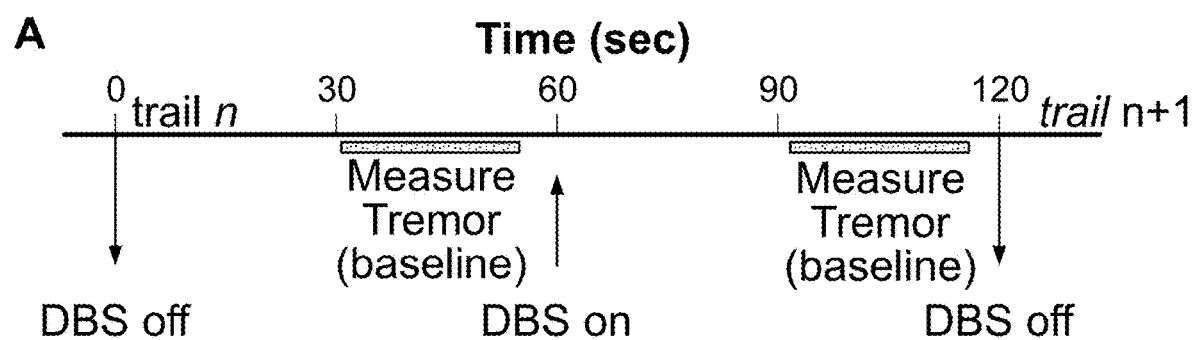
FIG. 28A is a graphical representation of a measure of an experimental tremor during a trial.

Tremor was measured in the contralateral limb during unilateral stimulation with a temporal pattern of stimulation generated according to the present invention having an average frequency of about 45 Hz, regular 45 Hz and 185 Hz stimulation, and with stimulation off (controls) in a single intraoperative session with a human subject. The stimulation pattern was presented to the subject, and the subject was blinded to the experimental condition. The trial began with one minute of stimulation off, with baseline tremor measured for 20 seconds beginning about 30 seconds into these intervals, and about 30 seconds after each condition was initiated experimental tremor was measured for 20 seconds (Ex. FIG. 28A).

Figure 28B:
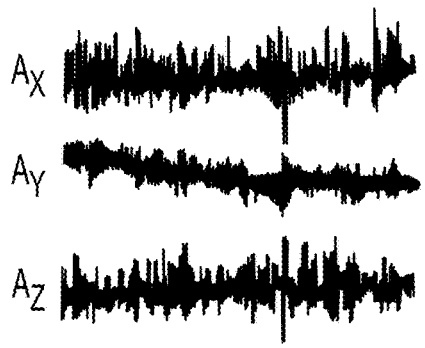
FIG. 28B is a graphical representation of amplitude of tremors with a power spectral density calculated for each of the measured amplitudes.
Figure 28B:
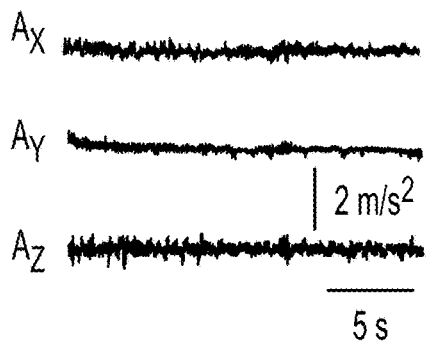
Figure 28B:
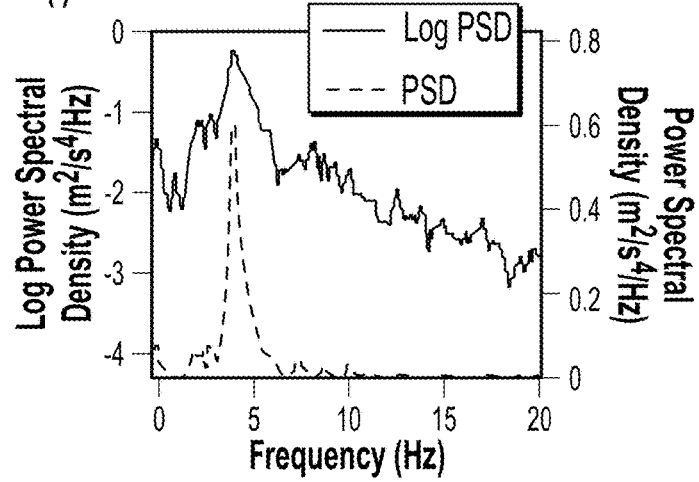
Figure 28B:
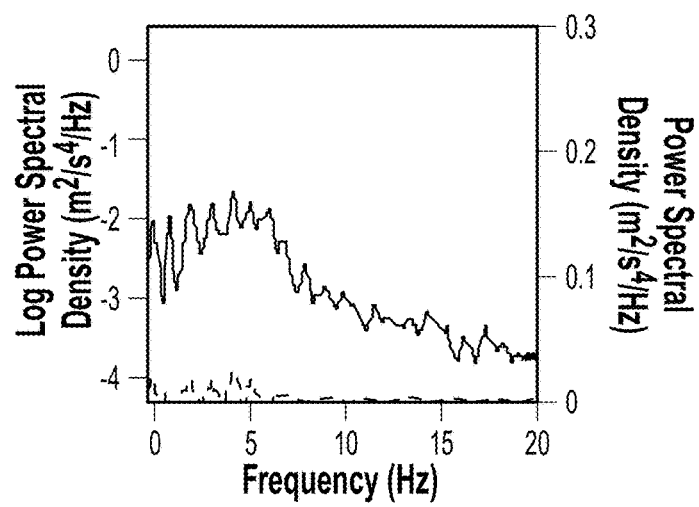

Tremor was measured using an accelerometer (Crossbow CXL04LP3; 5V/4 g sensitivity, San Jose, CA, USA) taped to the dorsum of the hand. The amplitude of tremor recorded by an accelerometer generally correlates well with clinical tremor rating scales. To obtain a single quantitative measure of tremor, the power spectral density was calculated for each of the three acceleration signals (AX, AY, and AZ, Ex. FIG. 28B) using the psd function (power spectral density, Welch's averaged periodogram, Hanning window, FFT length=5, 000) in MATLAB. Next, each spectrum was integrated from 2-20 Hz to get PX, PY, and PZ. Finally, PX, PY, and PZ were summed, and the log of the sum was calculated to get a single metric of tremor. The frequency range of 2-20 Hz was chosen to include the primary and several harmonics of the tremor and to exclude steady state acceleration due to gravity.

Figure 25:
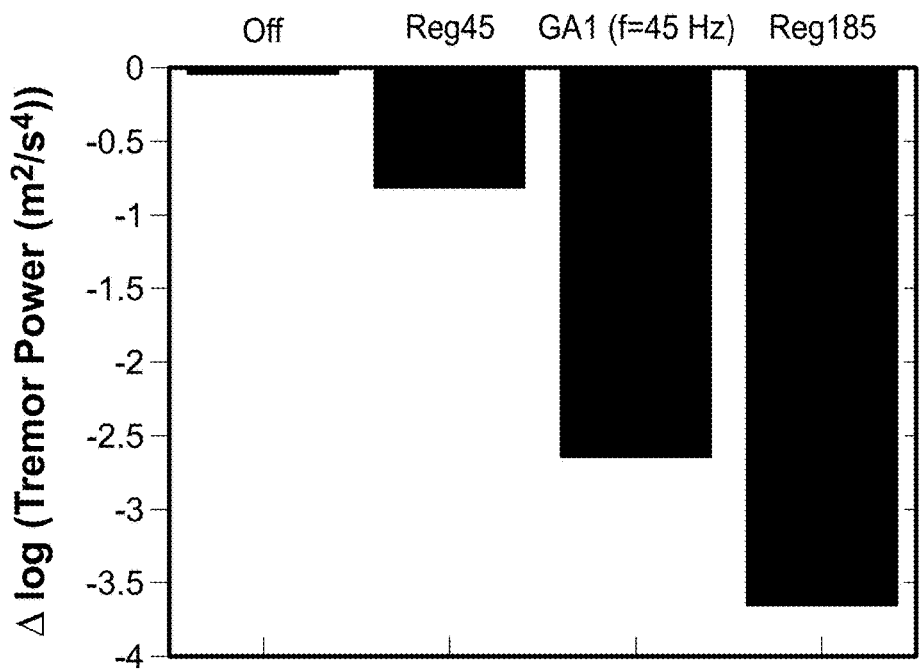
FIG. 25 is a graph of a quantitative measurement of the performance of the stimulation pattern of FIG. 20 as compared to other stimulation patterns in a human patient which had been diagnosed with PD and had tremor as a primary motor impairment related thereto.

As mentioned, the power spectral density for the acceleration signal was integrated from 2-20 Hz in order to get a single quantitative measure of the tremor amplitude. As can be seen in FIG. 25, the stimulation pattern generated according the present invention having an average frequency of about 45 Hz (GA1) reduced the tremor amplitude more than the regular 45 Hz stimulation but slightly less than regular 185 Hz stimulation. All three patterns of stimulation reduced tremor amplitude compared to the stimulation off condition.

Figure 26:
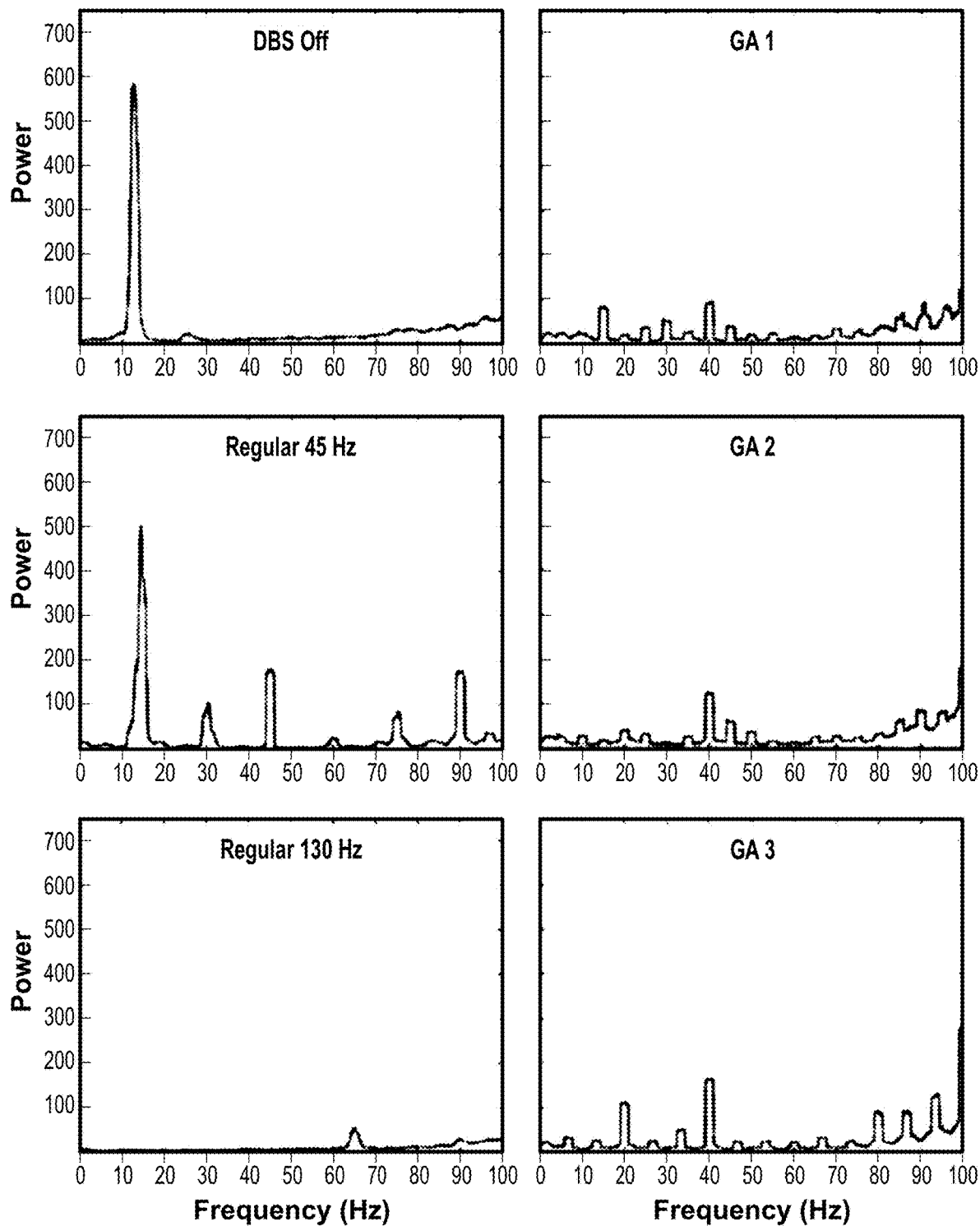
FIG. 26 includes graphs in the frequency domain of an average power of ten GPi neuronal firing sequences across a single iteration of the indicated stimulation, where such sequences were computer model generated.

FIG. 26 provides a spectral analysis of the average power across 10 GPi neurons for a single stimulation pattern iteration applying the indicated stimulation pattern to a forced Parkinsonian state in a model. As can be seen, there is significant oscillatory or synchronous activity generated around 15 Hz in the Parkinsonian state when the DBS input is off The 45 Hz regular interval stimulation does not lessen such activity much, but the 185 Hz regular interval stimulation does. Accordingly, there may be a correlation between an attenuation of such oscillatory or synchronous activity and the effectiveness of a given DBS stimulation pattern. Indeed, it has been observed that such attenuation is at least correlated to an improvement in movement, especially in animals that have a previously demonstrated or induced state of bradykinesia.

Figure 27:
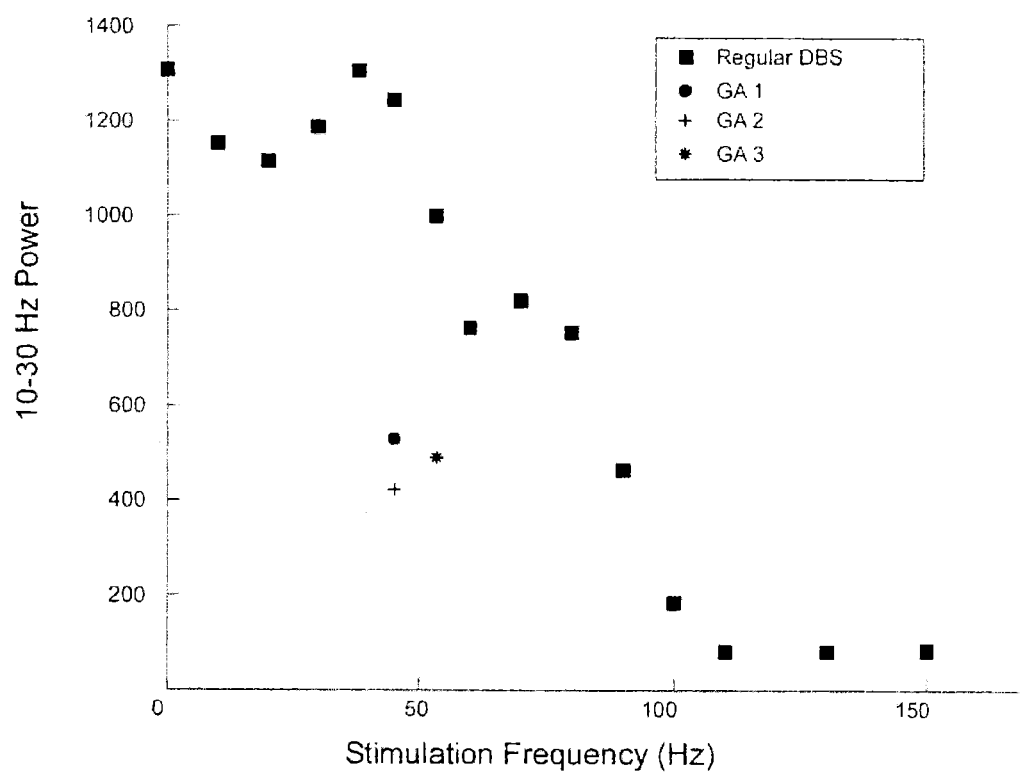
FIG. 27 is a tuning curve indicating the average power of ten GPi neuronal firing sequences across ten iterations of the indicated stimulation, where such sequences were computer model generated.

FIG. 27 provides an example tuning curve to analyze the 10-30 Hz global pallidus internal (GPi) neuronal power. That is, the spectra for 10 GPi neurons in a model were averaged for each stimulation state across 10 iterations. The plotted points indicate the average power of the GPi spike times across all 10 GPi neurons, averaged across the 10 stimulation iterations at each stimulation state. As can be seen, the power demonstrated in the 10-30 Hz frequencies by the GPi neurons (which are generally correlated to a neurological condition) is greatly reduced by the application of stimulation patterns that have been clinically shown to assist in reducing negative effects of such conditions. Accordingly, stimulation patterns according to the present invention may be, and have found to be, directed towards or involve the reduction of the average power of GPi oscillatory or synchronous activity. In fact, as shown in FIG. 27, an attenuation of at least about 25% of oscillatory activity caused by an actual animal neurological condition or a neurological condition model, but more preferably an attenuation of about 50% or greater, may be achieved using stimulation patterns according to the present invention.

The power of the oscillatory or synchronous activity that may be modeled, or measured from a patient, as correlated to a neurological condition may be used in alternative cost functions according to another embodiment of the present invention for optimizing stimulation patterns. One cost function that may be employed by an optimization algorithm or technique according to the present invention is as follows: $C=(P_{GA}-P_{FMReg})/P_{FMReg}*100\%$ where PGA is the average power generated by a computer model, over a given frequency range, of the firing of one or more GPi neurons when a selected generational stimulation pattern, which was initially created or generated by the genetic algorithm, is applied to the STN in the model and PFMReg is the power generated by a computer model, over the same given frequency range, of the firing the same GPi neurons when a DBS stimulation pattern of uniform frequency at a frequency equal to the average frequency of the GA train under analysis. The given frequency range may be a single frequency (e.g. 15 Hz) or a set of preferably contiguous frequencies (e.g. 10-30 Hz) or a set of noncontiguous frequencies (e.g. 15, 20, and 30 Hz).

Another cost function, using oscillatory power, that may be used to optimize stimulation patterns is as follows: $C=W*P+K*f$, where C is the cost, P is the average power generated by a computer model, over a given frequency range, of the firing of one or more GPi neurons when a selected generational stimulation pattern, which was initially created or generated by the genetic algorithm, is applied to the STN in the model, f is the average frequency of the generational pattern of stimulation, W is an appropriate weighting factor for the average power, and K is an appropriate weighting factor for the frequency. The given frequency range may be a single frequency (e.g. 15 Hz) or a set of preferably contiguous frequencies (e.g. 10-30 Hz) or a set of noncontiguous frequencies (e.g. 15, 20, and 30 Hz). The weighting factors W and K allow quantitative differentiation between efficacy (as a function of P) and efficiency (as a function of f) to generate patterns of non-constant inter-pulse interval deep brain stimulation trains that provide advantageous results with lower average frequencies, compared to conventional constant frequency pulse trains.

The non-regular temporal patterns of stimulation generated and disclosed above therefore make possible achieving at least the same, equivalent or superior clinical efficacy at a lower or comparable average frequency compared to conventional constant-frequency temporal patterns. The lower average frequencies of the non-regular temporal stimulation patterns make possible increases in efficiency and expand the therapeutic window of amplitudes and/or other stimulus parameters (e.g., pulse duration, and/or average frequency) that can be applied to achieve the desired result before side effects are encountered.

DBS is a well-established therapy for treatment of movement disorders, but the lack of understanding of mechanisms of action has limited full development and optimization of this treatment. Previous studies have focused on DBS-induced increases or decreases in neuronal firing rates in the basal ganglia and thalamus. However, recent data suggest that changes in neuronal firing patterns may be at least as important as changes in firing rates.

The above described systems and methodologies make it possible to determine the effects of the temporal pattern of DBS on simulated and measured neuronal activity, as well as motor symptoms in both animals and humans. The methodologies make possible the qualitative and quantitative determination of the temporal features of low frequency stimulation trains that preserve efficacy.

The systems and methodologies described herein provide robust insight into the effects of the temporal patterns of DBS, and thereby illuminate the mechanisms of action. Exploiting this understanding, new temporal patterns of stimulation may be developed, using model-based optimization, and tested, with the objective and expectation to increase DBS efficacy and increase DBS efficiency by reducing DBS side effects.

The invention provides non-regular stimulation patterns or trains that may create a range of motor effects from exacerbation of symptoms to relief of symptoms. The non-regular stimulation patterns or trains described herein and their testing according to the methodology described herein may facilitate the selection of optimal surgical targets as well as treatments for new disorders. The non-regular stimulation patterns or trains described herein may make possible improved outcomes of DBS by potentially reducing side effects, improving efficacy and/or prolonging battery life. The extended battery life may result from a lower average frequency of stimulation (45 Hz vs. 100 or 185 Hz), thereby delivering less electrical current over time. Surgeries to replace depleted pulse generators will be needed less frequently and the costs that a DBS patient can expect with the DBS system will be diminished.

Methods for Improving Efficacy of Treatment of Parkinson's Disease

The system 10 may be used to stimulate tissue of the central nervous system in patients with PD as a means of improving the efficacy of their treatment. A study was conducted with the system 10 and the results are as follows.

The efficacy of five temporal patterns of high frequency DBS was quantified using an alternating finger tapping task in human participants with PD. As well, the effect of each pattern on pathological beta band oscillations was quantified in a computational model of the basal ganglia.

Subject Information

In one study, individuals with DBS for PD undergoing implantable pulse generator (IPG) replacement surgery were tested. Subjects were at least three months post DBS electrode implant/revision, capable of performing a simple finger tapping task, neurologically stable, and capable of understanding the study and consent form. Ten subjects completed the protocol and were analyzed. DBS electrode target nucleus was either STN (7/10) or GPi (3/10). Subjects were asked to withhold PD medications for 12 hours prior to surgery, and most (7/10) complied.

Intraoperative Stimulation Protocol

Sedation and analgesia were withheld when possible (8/10) and local anesthetic (lidocaine) was used. Following removal and disconnection of the depleted 1PG, a sterile connection was made between the extension cable and the signal generation equipment, allowing different temporal patterns of stimulation to be delivered through the implanted electrode.

Custom software (LabVIEW) on a battery-powered laptop computer generated the experimental patterns of stimulation. The analog voltage outputs (DAQCard™6062E) were optically isolated (bp Optical Isolator with Probe) from the stimulation hardware. The subject's clinical stimulation parameters and contact settings were maintained when possible. Subjects with case (+) programming (4/10) were switched to a bipolar configuration and one of the clinically inactive electrode contacts was set as (+). Subjects (4/10) occasionally experienced uncomfortable side effects when the clinical DBS amplitude was applied-presumably because their clinical stimulation parameters were adjusted as the IPG battery voltage declined-and the maximum stimulation amplitude that did not cause discomfort was used. Some patients reported paresthesias from stimulation, but there were no other adverse events.

Stimulation Patterns

Figure 29A:
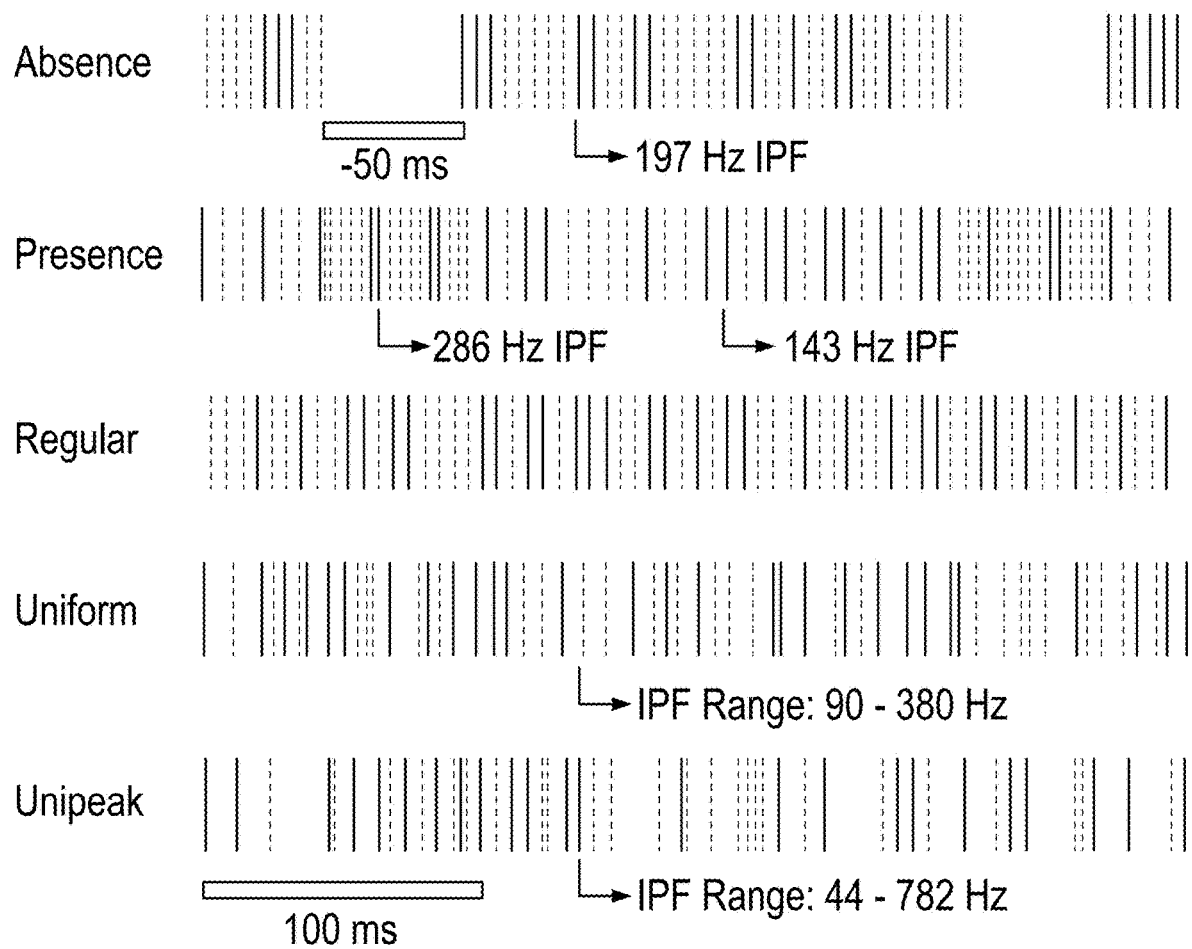
FIG. 29A is a diagrammatic trace that shows a temporal pattern of DBS with instantaneous pulse frequency (IPF) values and ranges labeled.

Bradykinesia during DBS-off (Baseline) was compared to temporally regular DBS at 185 Hz (Regular) and to four non-regular temporal patterns of DBS (FIG. 29A) named according to their dominant feature or the shape of their instantaneous pulse frequency (IPF) distribution. The Absence and Presence patterns were both periodic with low entropy <<1 bits/pulse) and characterized by either short periods absent of pulses or the presence of short bursts of pulses, respectively. The pauses and bursts both occurred at 4.4 Hz. The Uniform and Unipeak patterns were highly irregular (high entropy: –5.5-5.6 bits/pulse) and were created from log-uniform distributions of IPFs. Although the Unipeak pattern was created from a wider log-uniform distribution of IPFs (44-720 Hz) than the Uniform pattern (90-360 Hz), the two patterns had the same entropy.

Motor Performance Measurements

Figure 29B:
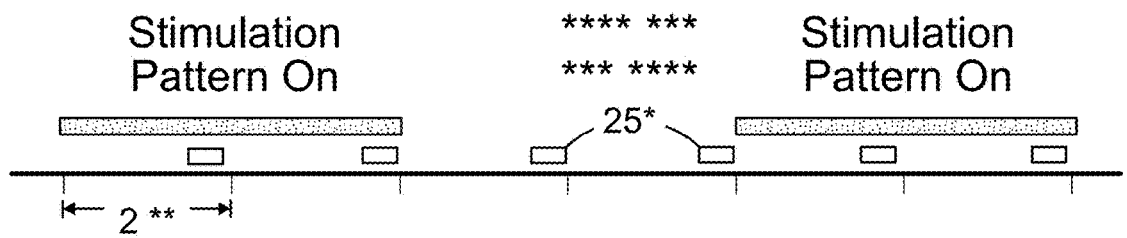
FIG. 29B is a representation of an intraoperative experiment timeline.
Figure 29C:
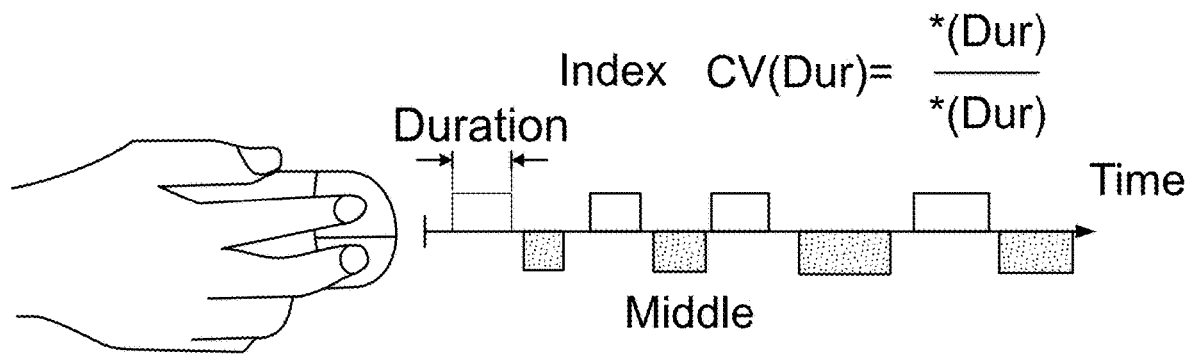
FIG. 29C is a representation of motor performance as quantified during an alternating click task on a two-button computer mouse using a measure of tap duration (Dur) variability.
Figure 29D:
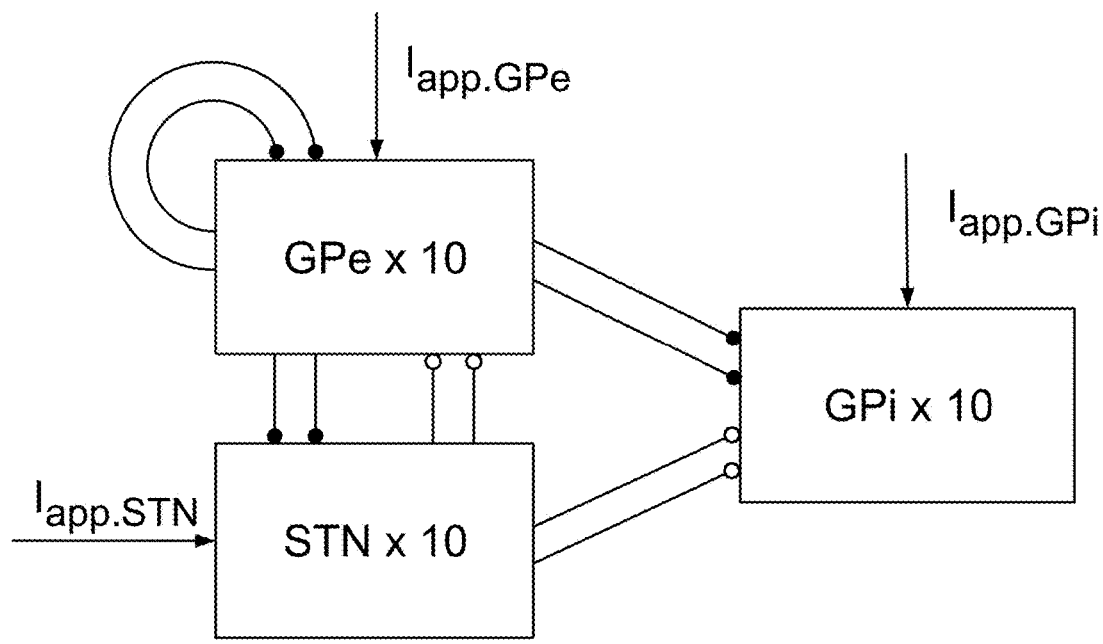
FIG. 29D is a representation of the structure of the computational model of the basal ganglia, which exhibited oscillatory activity in the beta frequency range.

Motor performance was quantified using an alternating finger tapping task. The subject's hand contralateral to stimulation was placed on a two-button computer mouse and the subject was asked to press alternately each button during 20 second trials repeated every two minutes (FIGS. 29B and C).

The log-transformed coefficient of variation of tap duration is a statistical measure of variability of tap duration that is significantly correlated with the Unified Parkinson's Disease rating scale (UPDRS) motor score, particularly with the bradykinesia subscore, and was the primary measure of motor task performance across stimulation conditions. Because of the time course of the effects of DB5 on motor symptoms in PD, the second data collection epoch near the end of each stimulation condition was analyzed unless it was missing, in which case the first data collection epoch served as its replacement. Furthermore, only button presses made with the index finger were analyzed because experimenter observations, post-hoc data analysis, and further analysis of previously published data used to validate the alternating finger tapping task revealed that this was a more robust outcome measure. The same trends in the data were observed when averaging index finger motor performance during the early and late data collection epochs and when averaging the motor performance during the early and late data collection epochs for both fingers separately. In this repeated measures experimental design, bradykinesia in subjects at Baseline (DBS off) and during all five stimulation patterns was quantified. After the Baseline condition, the order of stimulation pattern presentation was randomized for each patient, and subjects were blinded to the stimulation conditions. After completing the experimental protocol, the sterile connection between the extension cable and the stimulus-generating equipment was disengaged, and the IPG replacement surgery was completed.

Data Analysis and Statistics

Data collected through LabVIEW were processed using custom scripts in MATLAB R2009b to extract click durations from the alternating finger tapping task. Technical outliers were removed by discarding extremely short clicks that were artifacts of the computer mouse clicking apparatus (debouncing). JMP 9 and StatView 5.0.1 for Windows were used to conduct the statistical analyses. Experimental data were analyzed using repeated measures analysis of variance (ANOVA) with log-transformed coefficient of variation of the index finger tap duration as the repeated measure in each subject. The log-transformed coefficient of variation of the index finger tap intervals and the log-transformed number of index finger taps per 20 s data collection epoch are alternative motor performance measures that were also analyzed using the repeated measures ANOVA model. Fisher's protected least significant difference (PLSD) test was used to make post-hoc comparisons across experimental conditions. Pearson's correlation coefficient was used to assess correlation strength. Paired t-tests were performed to access the effects of bursts, pauses, and irregularity, per se, in data that were pooled across stimulus condition. Statistical significance was defined at $a=0.05$.

Computational Model of the Basal Ganglia

A biophysical model of the basal ganglia in a PD state was used to determine the effect of the different patterns of stimulation on oscillatory activity in model neurons. The computational model included the STN, GPi, and external globus pallidus (GPe), and each nucleus contained 10 single compartment neurons. Each GPe neuron sent inhibitory projections to two STN neurons, two GPi neurons, and two other GPe neurons. STN neurons sent excitatory projections to two GPe neurons and two GPi neurons (FIG. 1D). The biophysical properties of each neuron type were validated against experimental data, and are described in detail elsewhere. Constant currents were applied to neurons in each nucleus to represent inputs from afferent projections that were not included in the model and produced firing rates that were consistent with observations in non-human primate models of PD and human patients with PD. STN and GPi neurons received applied current of 33~/cm2 and 21~cm2, respectively. Variability was added to the model by delivering a constant current to each GPe neuron randomly drawn from a normal distribution centered around 8~/cm2 with a standard deviation of 2~/cm2. STN DBS was applied by delivering the desired pattern of current pulses (amplitude 300~/cm2; pulse width 0.3 ms) to each STN neuron. Simulations were implemented in MATLAB R2009b with equations solved using the forward Euler method with a time step of 0.01 ms and a total simulated time of 20 s.

Neurons in all nuclei exhibited strong oscillatory activity in the beta frequency range centered around 20 Hz. Beta band oscillatory activity is implicated in the pathophysiology of PD. Therefore, the effect of different stimulation patterns on the oscillatory activity in the primary output nucleus of the basal ganglia, the GPi, was quantified. Spectrograms of the GPi spike times were generated using the Chronux neural signal analysis package and MATLAB R2009b. The average multitaper spectrograms from GPi spike time data across all 10 GPi neurons using a 2 s sliding window and a 0.1 s step size was calculated. Since the frequency of the oscillatory activity could change over time as the stimulation was delivered, the beta band power was quantified by evaluating the time-integral of the peak power density in the beta frequency range (13-35 Hz). These values were log-transformed and termed Beta Band Power.

Results

Figure 30A:
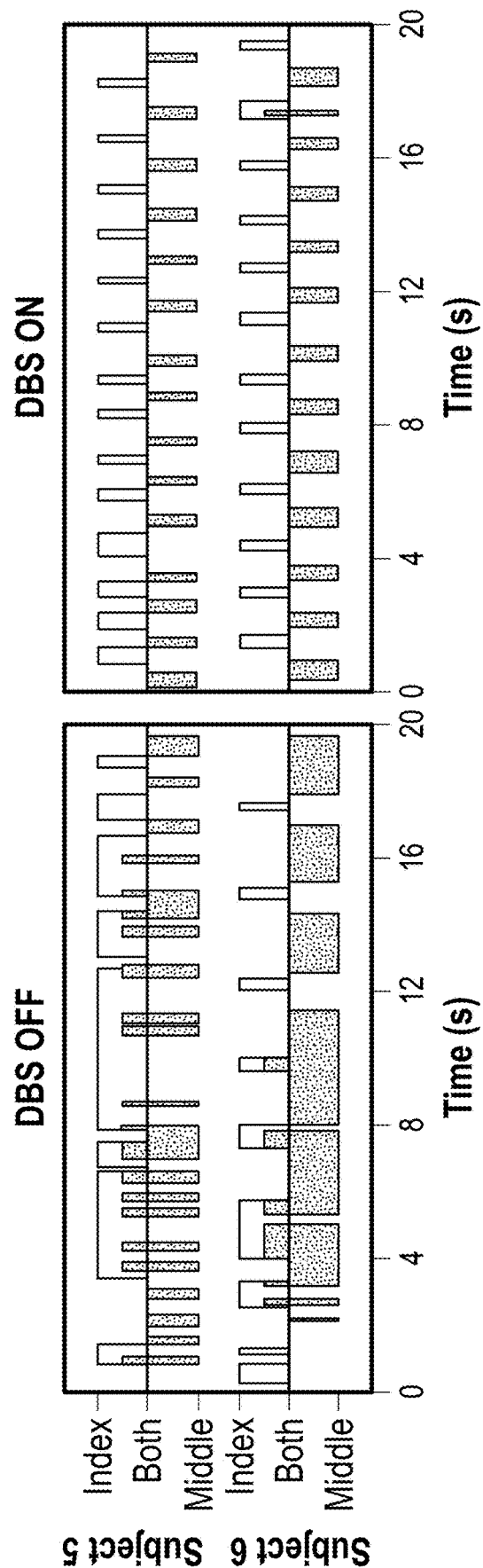
FIG. 30A is a diagrammatic trace that compares Baseline (DBS off) finger tapping to finger taping during DBS.
Figure 30B:
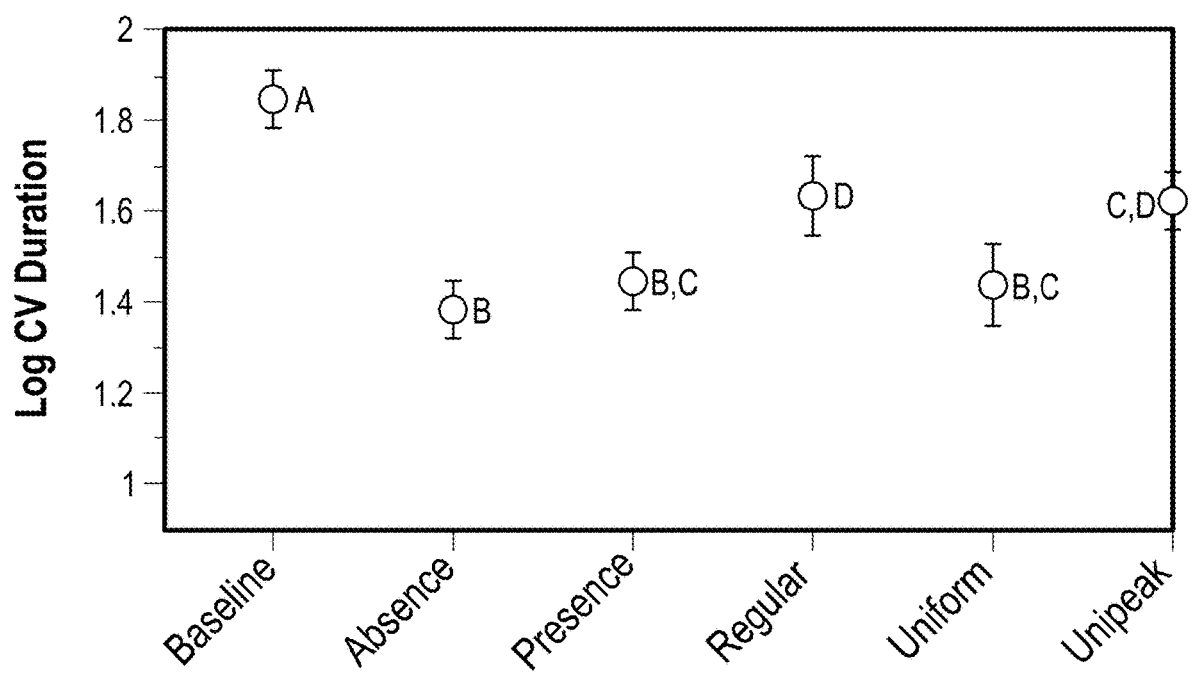
FIG. 30B is a graphic representation showing mean+ s.e.m. log-transformed coefficient of variation of tap durations (log CV Duration) across all stimulation conditions.

Bradykinesia was measured in subjects with PD while applying different temporal patterns of DBS to determine which characteristics of non-regular stimulation influenced its efficacy. Motor performance was quantified using the log-transformed coefficient of variation of index finger tap duration (Log CV Duration) during alternating finger tapping, and DBS improved performance in this task (FIG. 30). Repeated measures ANOVA revealed that the variability of finger tap duration was dependent on the pattern of DBS ($F=7.989$, $P<0.001$). In accordance with previous studies showing that DBS ameliorates motor symptoms in PD, post-hoc testing revealed that tap duration variability was greater during Baseline (DBS off) compared to Regular DBS ($p=0.016$). Furthermore, tap duration variability was greater during Baseline compared to all the applied patterns of DBS individually ($p<0.05$), indicating that all patterns of stimulation improved motor performance compared to the DBS off condition.

Post-hoc testing also revealed significant differences between stimulation patterns. During Absence, Presence, and Uniform DBS, the tap duration variability was lower than during Regular DBS ($p=0.007$, $p=0.031$, and $p=0.028$, respectively), indicating that these patterns improved bradykinesia in PD more effectively than the temporally regular stimulation pattern used clinically. Motor task performance (Log CV Duration) during the Unipeak and Regular patterns was similar. Consequently, tap duration variability during the Absence, Presence, and Uniform stimulation patterns was lower than during the Unipeak pattern ($p=0.018$, $p=0.069$, and $p=0.063$, respectively). When individually added to the repeated measures ANOVA statistical model, there was not a significant effect of surgical target (GPi and STN: $p=0.21$), medication state ($p=0.42$), sedation status ($p=0.54$), or switching to a bipolar electrode configuration ($p=0.75$).

The responses to the different temporal patterns of stimulation were consistent across subjects. In 9/10 subjects, motor performance was better during the Absence and Uniform patterns compared to the Regular pattern. Motor performance was superior during Presence DBS compared to Regular stimulation in 7/10 subjects. Motor performance was improved during stimulation compared to Baseline in 80-100% of the subjects depending on the pattern.

Figure 31A:
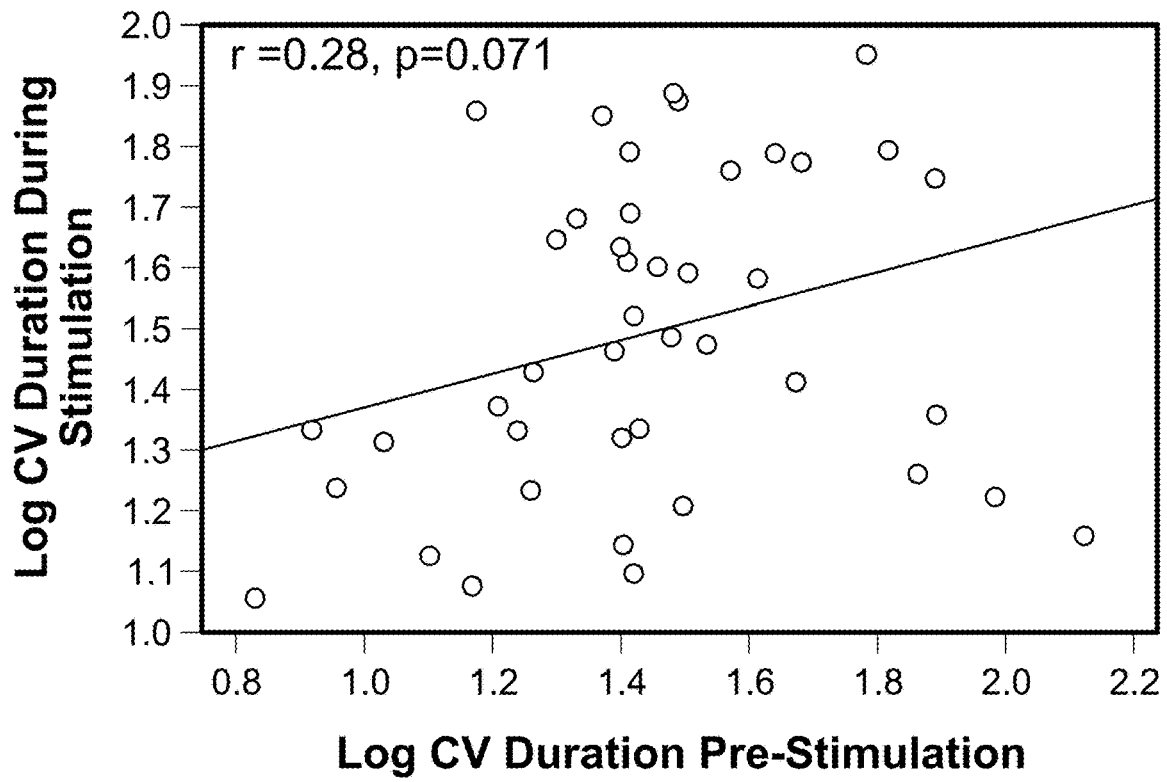
FIG. 31A is a graphical representation showing motor performance during stimulation is weakly correlated with motor performance during the preceding stimulation off-period.
Figure 31B:
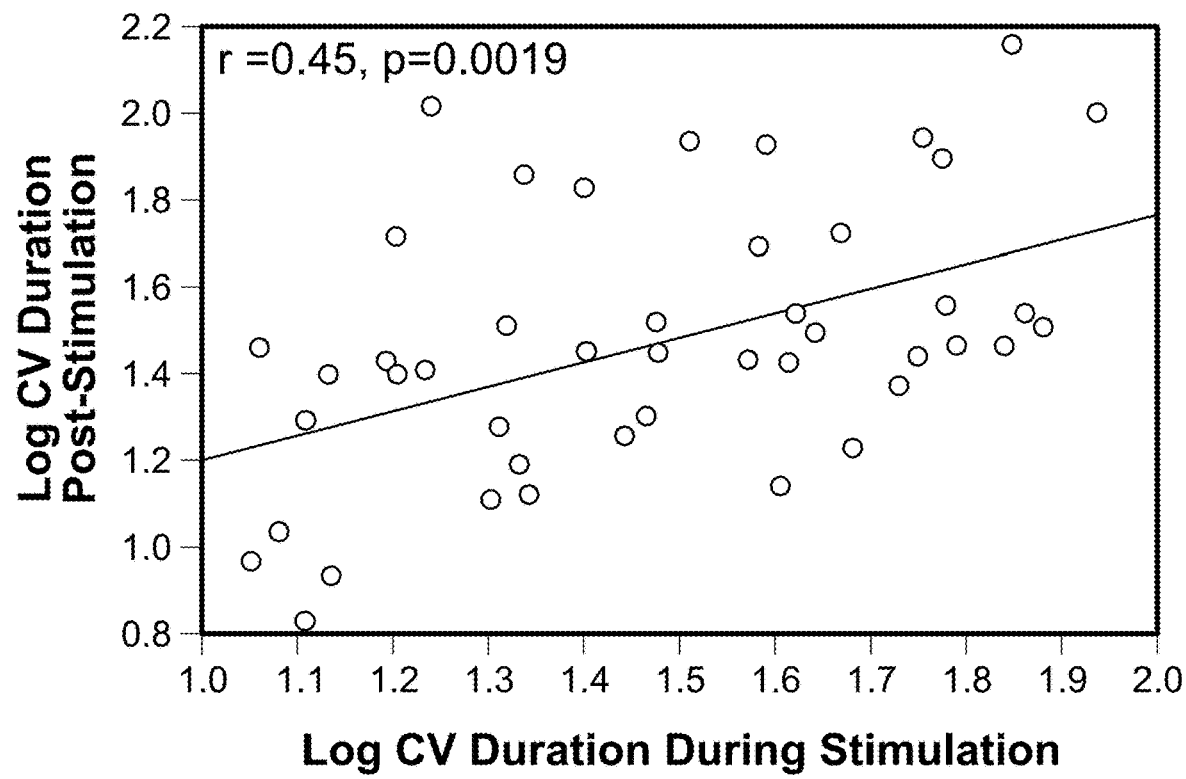
FIG. 31B is a graphical representation showing that motor performance during stimulation is significantly correlated with motor performance during the following stimulation off-period.

Motor performance during the stimulation patterns was weakly correlated ($p=0.071$, $R2=0.076$) with motor performance during the stimulation off period immediately preceding when the stimulation pattern was applied (FIG. 31A). This suggested that changes in finger tap duration variability between stimulation patterns were caused by the stimulation patterns themselves, and were not a reflection of fluctuations in baseline motor performance. Instead, and consistent with the time course of the action of DB5 in PD, motor performance during the stimulation off period following each stimulation pattern reflected the motor performance during the preceding pattern of stimulation, as demonstrated by significant correlations between finger tap duration variability during the stimulation pattern and during the subsequent stimulation off periods (p=0.0019, R2=0.20; FIG. 31B).

Figure 32A:
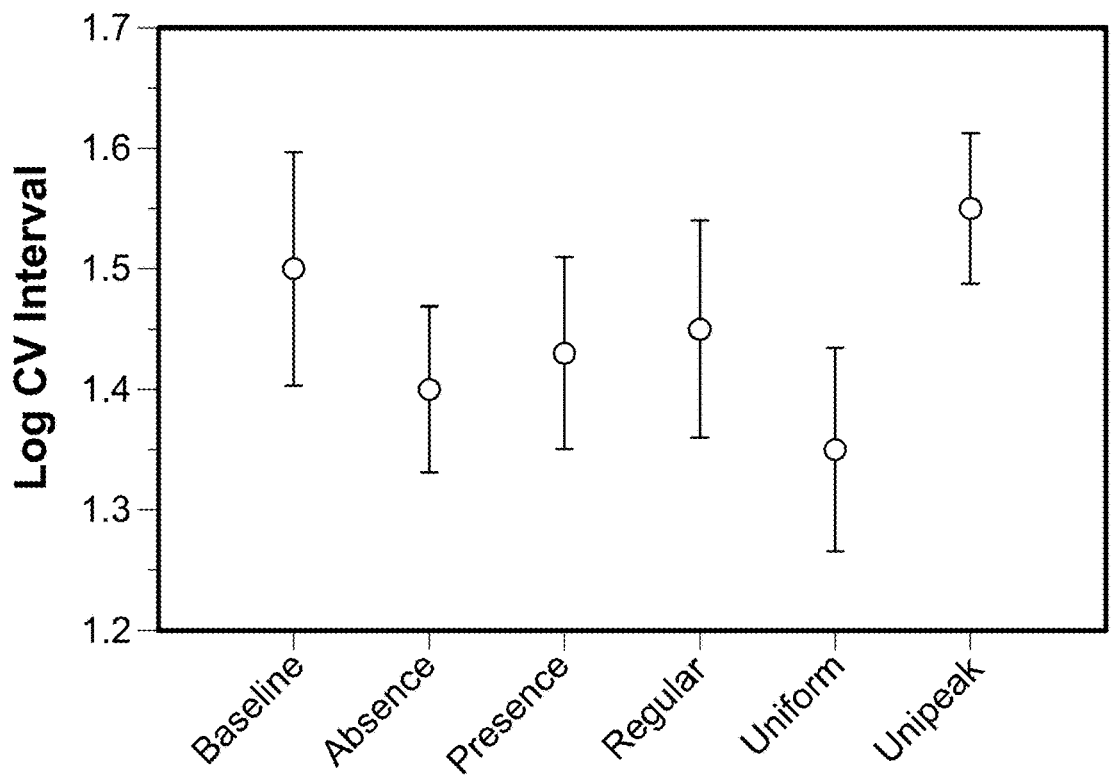
FIG. 32A is a graphical representation showing mean+ s.e.m. log-transformed coefficient of variation of the intervals between taps (log CV Interval) across all stimulation conditions.
Figure 32B:
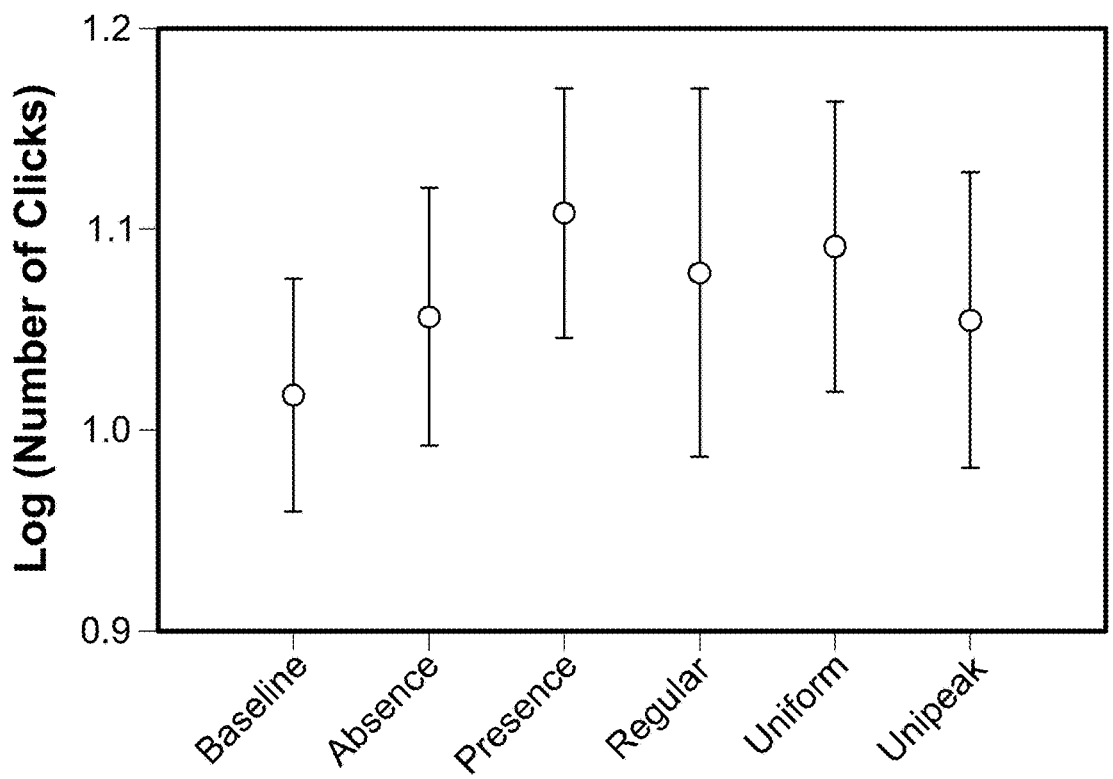
FIG. 32B is a graphical representation showing of mean+ s.e.m. log-transformed number of clicks per 20 s data collection epoch across stimulation conditions.

The log-transformed coefficient of variation of the intervals between finger taps (log OJ Interval) exhibited the same pattern of motor performance across stimulation patterns as log CV Duration (FIG. 32A). The finger tap timing was the most irregular, on average, during Baseline and the Unipeak pattern of stimulation, and the average log CV Interval during Absence, Presence, and Uniform DBS was lower than it was during Regular DBS. However, average differences in log CV Interval across patterns of stimulation were small, and the repeated measures ANOVA did not reveal a statistically significant effect of DB5 pattern (p=0.44). The log-transformed rate of finger tapping exhibited a similar dependence on stimulation pattern. The fewest button presses occurred during Baseline (stimulation off), and the most occurred during the Presence pattern of stimulation (FIG. 32B). However, the mean differences in tapping rates between the patterns of stimulation were small relative to the variance, and the repeated measures ANOVA did not reveal a significant effect of DB5 pattern (p=0.45).

Figure 33A:
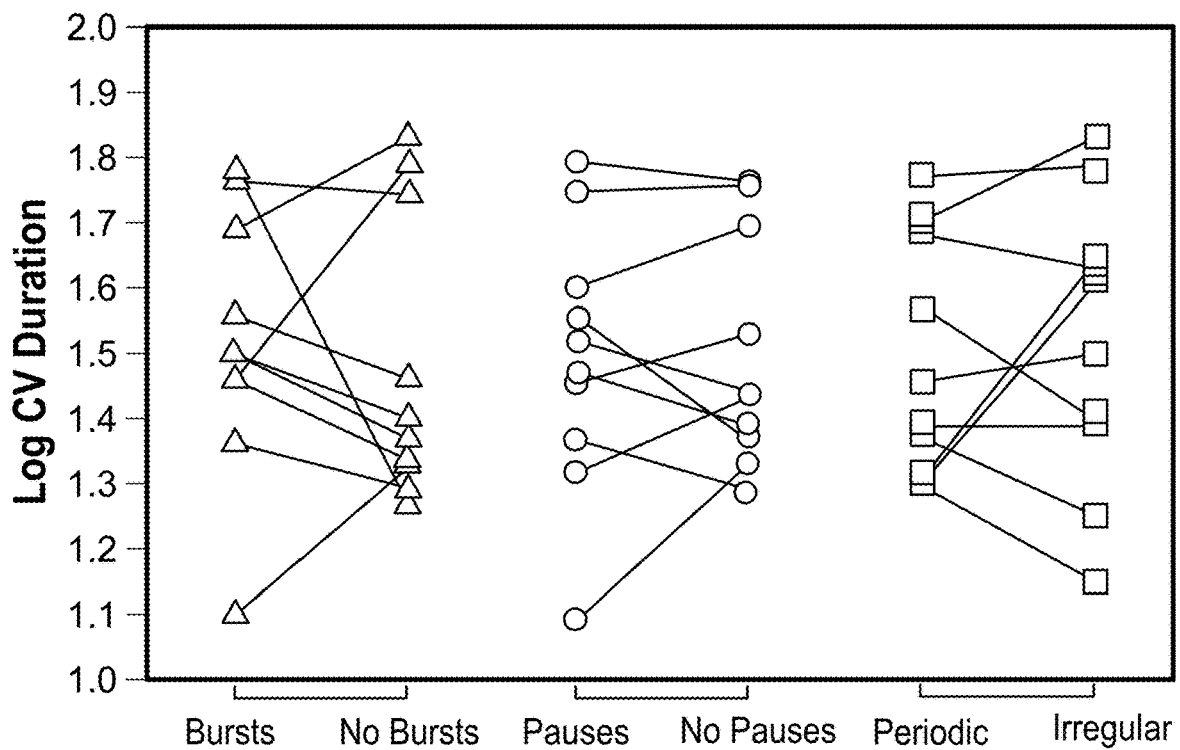
FIG. 33A is a graphical representation showing the effects of bursts, pauses, and irregularity in the stimulation patterns with respect to log CV Duration.
Figure 33B:
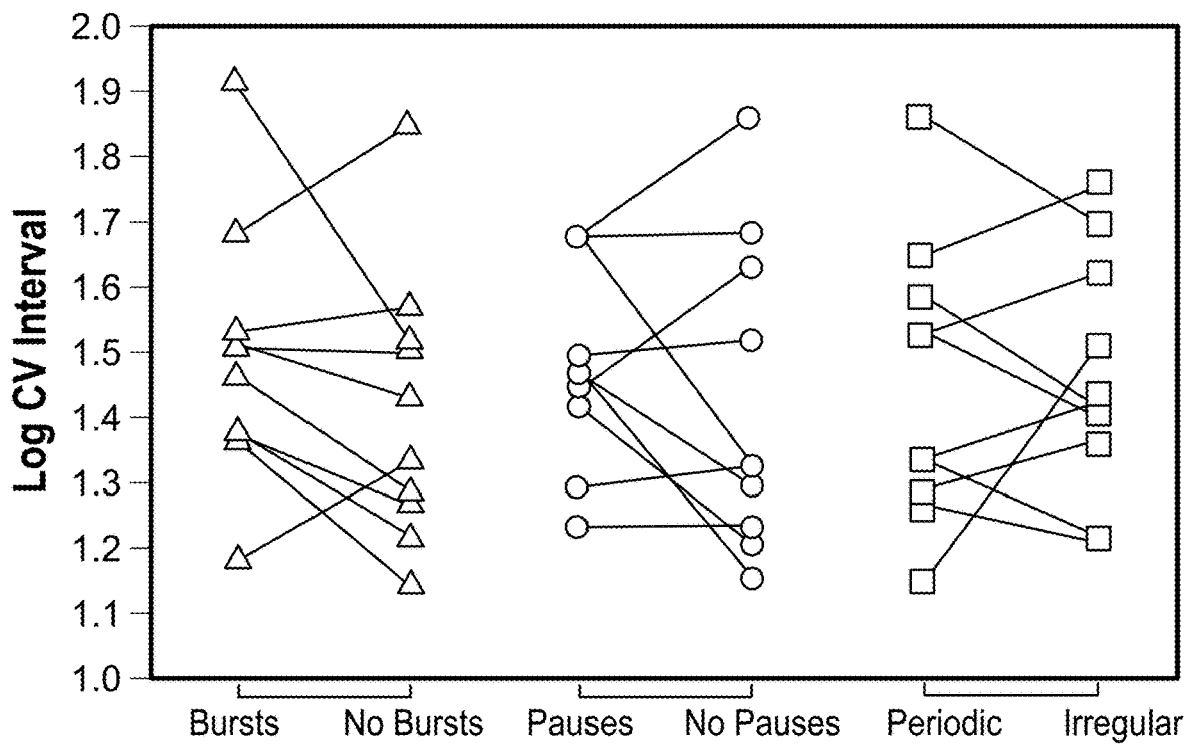
FIG. 33B is a graphical representation showing the effects of bursts, pauses, and irregularity in the stimulation patterns with respect to log CV Interval.
Figure 33C:
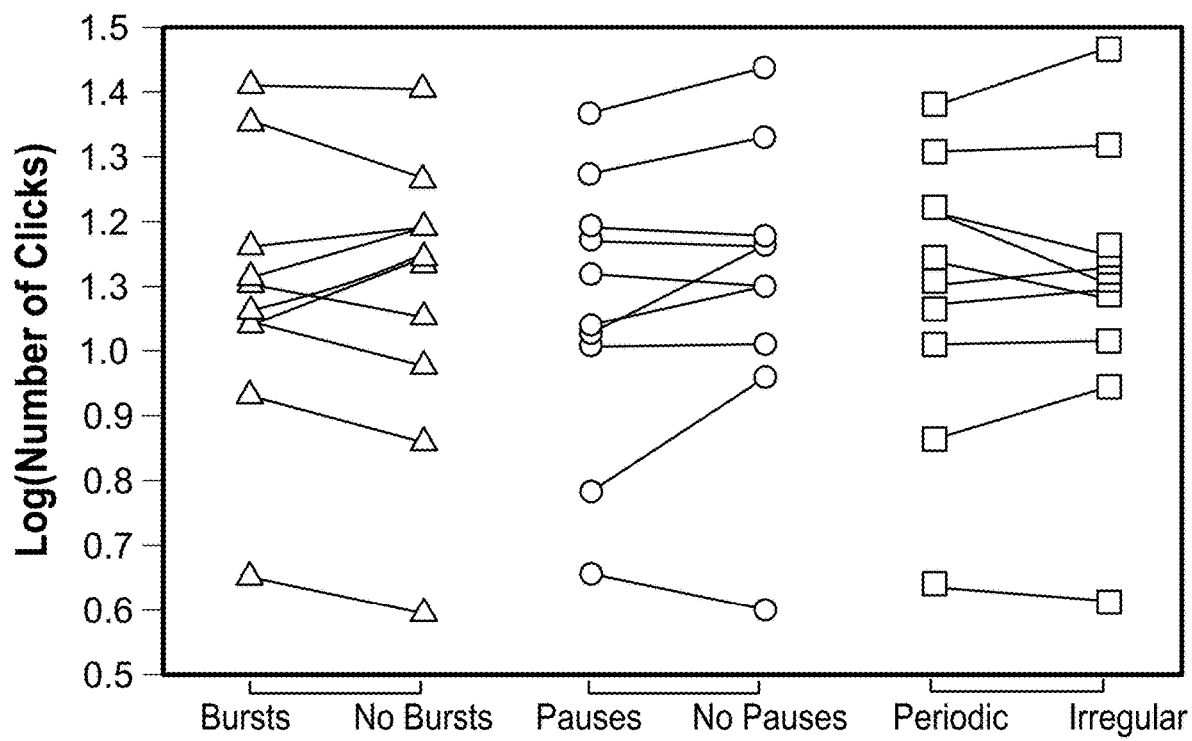
FIG. 33C is a graphical representation showing the effects of bursts, pauses, and irregularity in the stimulation patterns with respect to tapping rate.

Some temporal patterns of DBS improved motor performance more than regular stimulation, but the original goal was to determine which features of the stimulation patterns influenced the efficacy of DBS. Therefore, the effects of bursts, pauses, and irregularity in the stimulation patterns by pooling motor performance data across stimulation trains that shared the feature of interest were measured. The data was pooled during Presence and Unipeak DBS into a "Bursts" group and the remaining patterns into a "No Bursts" group; measurements made during Absence and Unipeak DBS were pooled into the "Pauses" group; and measurements from Uniform and Unipeak DBS were pooled into the "Irregular" group. Paired t-tests did not reveal a significant effect of bursts, pauses, or irregularity on the log CV Duration (FIG. 33A), log CV Interval (FIG. 33B), or tapping rate (FIG. 33C).

It is possible that the effects of different temporal patterns of stimulation were explained by statistical properties of the patterns rather than being a direct result of the patterns themselves. However, there were no significant correlations between mean log CV Duration and several statistical descriptors of the stimulation patterns including the pattern maximum IPF (p=0.53)' mean IPF (p=0.G2), mean pulse rate (p=0.82), or entropy (p=0.87).

Figure 34A:
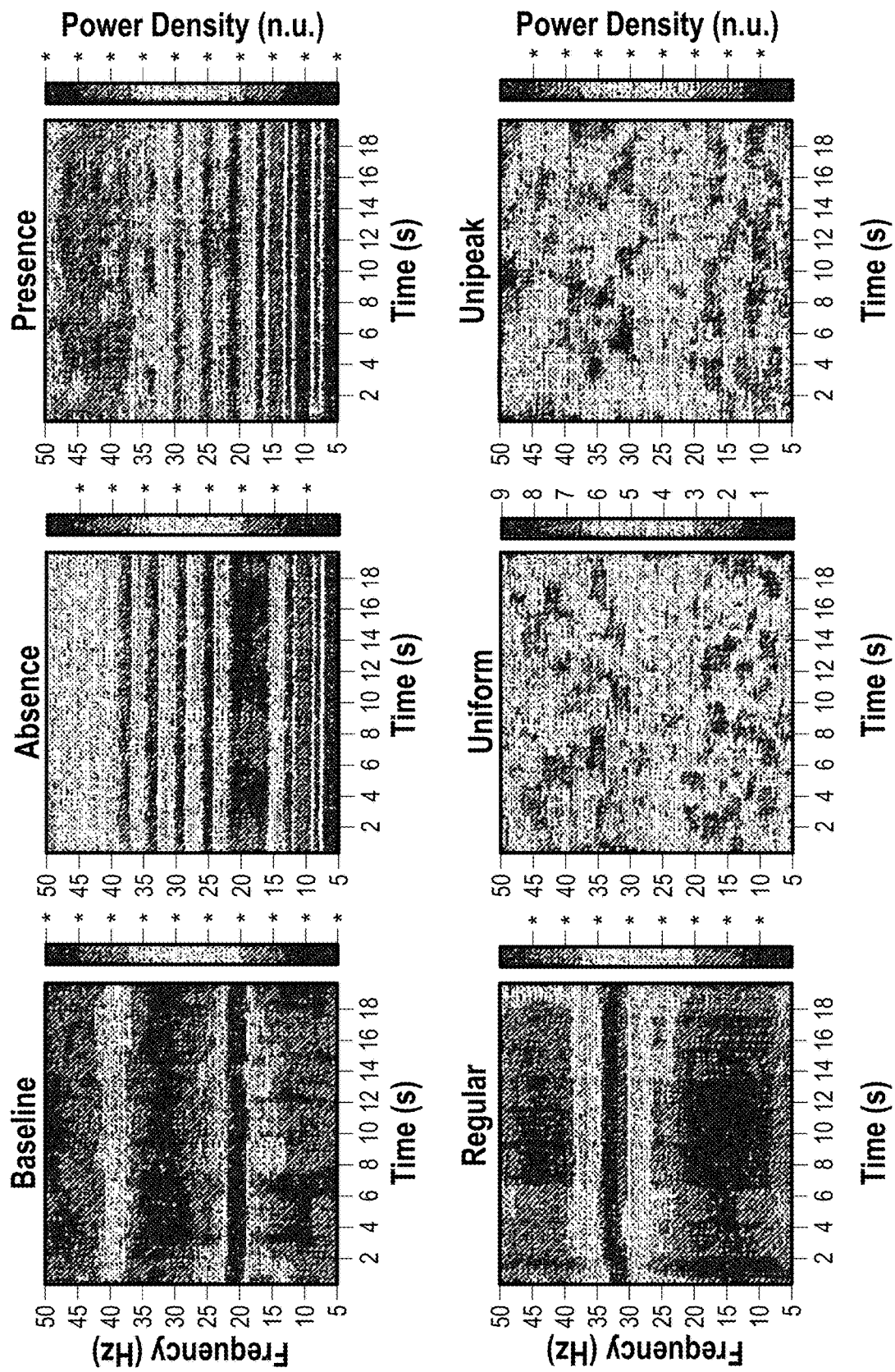
FIG. 34A is a spectrogram showing GPi spike times from the computational model of the basal ganglia in the PD state across stimulation conditions.
Figure 34B:
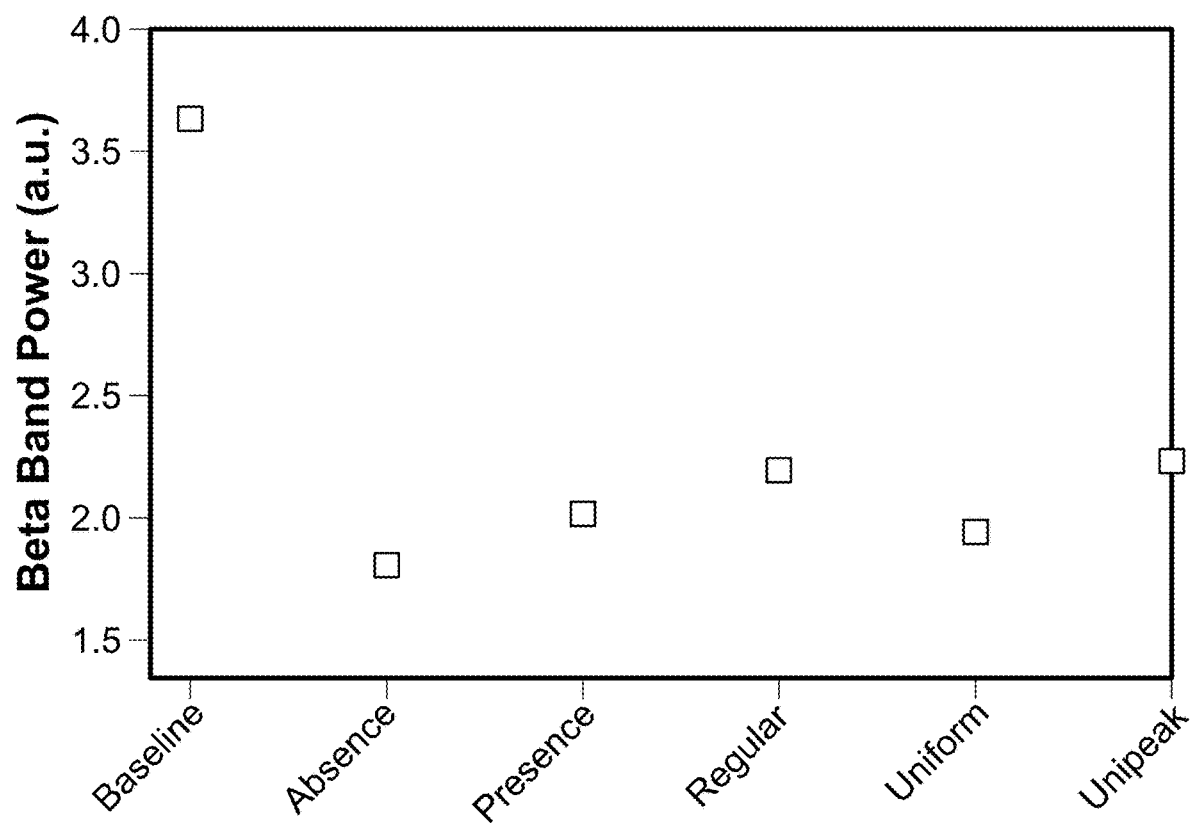
FIG. 34B is a graphical representation showing that a log-transformed time-integral of the average GPi spike time peak power density in the beta frequency range across stimulation conditions is strongly correlated with log CV Duration.
Figure 34C:
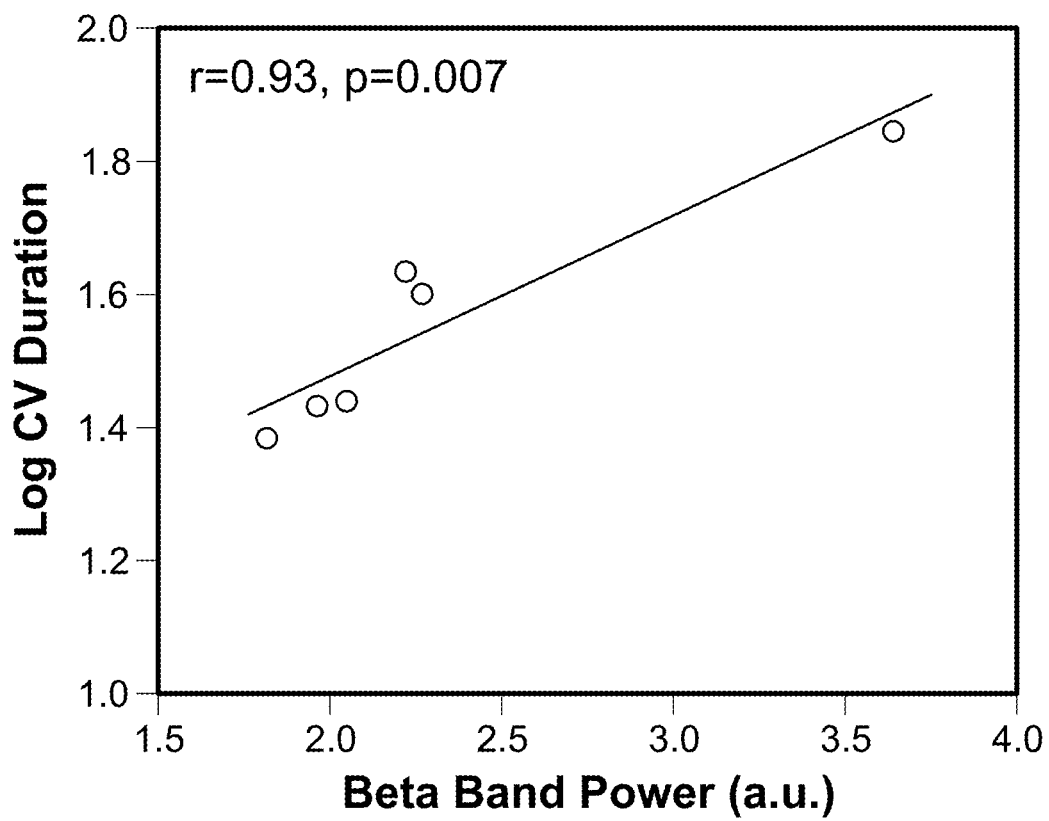
FIG. 34C is a graphical representation showing that a log-transformed time-integral of the average GPi spike time peak power density in the beta frequency range across stimulation conditions is strongly correlated with log CV Duration.

A biophysical model of STN-DBS was used to quantify the effects of different temporal patterns on beta band oscillations in the model GPi. The averaged multitaper spectrograms from the GPi spike time data revealed prominent oscillatory activity that was suppressed by DBS (FIG. 34A). All DBS patterns suppressed Beta Band Power compared to Baseline, and the relative effects of different patterns on Beta Band Power mirrored their effects on the experimental measures of motor function (FIG. 34B). Indeed, there was a strong correlation (p=0.007, R2=0.87) between Beta Band Power and log CV Duration (FIG. 34C). Furthermore, Absence, Presence, and Uniform DBS suppressed Beta Band Power more than Regular and Uniform DBS.

Discussion

Quantitative measurement of the effects of different temporal patterns of DBS on bradykinesia in subjects with PD and oscillatory activity of model neurons revealed three central findings. First, the pattern of stimulation, and not simply the stimulation rate, was an important factor in the clinical efficacy of DBS, as demonstrated by the different levels of performance on a simple motor task during different temporal patterns of stimulation all of which had the same mean frequency. Second, some non-regular patterns of stimulation relieved motor symptoms in PD more effectively than the temporally regular stimulation pattern used clinically. Third, the differential efficacy of DBS patterns was strongly correlated with the pattern's ability to suppress pathological oscillatory activity in the basal ganglia (FIG. 34C).

The log-transformed coefficient of variation of tap duration is significantly correlated with the bradykinesia subscore of the UPDRS, suggesting that the quantitative intraoperative measurements may be predictive of functional change. Secondary motor performance outcome measures (log CV Interval and log-transformed number of clicks) supported the primary motor performance outcome measure (log CV Duration). The correlation between log CV Interval and UPDRS motor scores is weaker than the correlation between log CV Duration and UPDRS motor scores. The rate of finger tapping can also be used to quantify motor performance during an alternating finger tapping task, and it has also been correlated with UPDRS motor scores. Although statistically significant differences in secondary motor performance measures were not observed, the data mirrored the log CV Duration data remarkably well. There were, however, two discrepancies of note. First, performance quantified by the log CV Interval during Unipeak DBS was poor. In fact, according to this measure, it was slightly worse than motor task performance during Baseline. Second, the tapping rate data indicate that fewer clicks occurred during Absence DBS than during Regular DBS. Therefore, this contradicts that motor task performance— quantified by the tap duration variability—during Absence DBS was significantly better than during Regular DBS.

Oscillatory and synchronized neural activity in specific frequency bands appear to be related to motor performance in patients with PD, and the non-regular patterns of stimulation that were most effective may be most able to override or otherwise disrupt pathological oscillations or synchronization in the basal ganglia. Indeed, the degree of suppression of the oscillatory activity in the model neurons matched the clinical efficacy of the patterns during the finger tapping task remarkably welt suggesting that the efficacy of these patterns of DBS depended on their ability to suppress, disrupt, or otherwise regularize pathological activity in the basal ganglia.

Conducting experiments during the IPG replacement surgery uniquely enabled the present experiments by enabling direct connection to the brain lead. Patients had a stable electrode-tissue interface, clinically relevant contact selections, and stimulation parameters with demonstrated clinical efficacy. Performing these experiments during the DBS lead implantation surgery, between the lead implant and the IPG implant, or in the immediate postoperative period is undesirable because of unproven clinical efficacy and transient effects of electrode implantation. However, the intraoperative setting limited trial durations, so the effects of the patterns of stimulation may not be fully developed and differences across patterns may be underestimated. A finger tapping task was used with quantitative measures that are correlated with UPDRS motor scores. The correlations between log CV Durations and the bradykinesia and rigidity UPDRS motor subscores are significant, but it remains unclear whether these non-regular patterns of stimulation would ameliorate other Parkinsonian motor signs.

There is evidence from many systems supporting the importance of temporal pattern in determining the effects of stimulation. Taste sensation differed across patterns of stimulation of the rat brainstem, even if the patterns had the same average frequency. Temporal patterns of intra-cortical microstimulation can encode artificial tactile information in monkeys using a brain-machine-brain interface. There is also other evidence that non-regular stimulation patterns could be more effective than regular stimulation for the treatment of movement disorders. In an adult rhesus monkey rendered Parkinsonian with 1-methyl-4-phenyl-1,2,3,6tetra-hydropyridine (MPTP), burst stimulation patterns similar to the Absence and Presence DBS patterns improved movement times relative to frequency-matched regular stimulation. As well, closed-loop temporally non-regular stimulation cued from physiological signals outperformed regular DBS in a MPTP primate model of PD. In combination with the present findings, there is compelling evidence that non-regular temporal patterns of stimulation could be more effective than regular stimulation.

The present results highlight the importance of the temporal pattern of stimulation as a means to enhance the efficacy of DBS to treat PD. Non-regular high frequency stimulation can improve bradykinesia in patients with PD more effectively than clinically-available temporally regular stimulation by more thoroughly suppressing or disrupting pathological oscillatory activity in the basal ganglia.

The foregoing is considered as illustrative only of the principles of the invention. Furthermore, since numerous modifications and changes may readily occur to those skilled in the art, it is not desired to limit the invention to the exact construction and operation shown and described. While the preferred embodiment has been described, the details may be changed without departing from the invention. For instance, although the disclosed embodiments of an algorithm used to generate stimulation patterns is an evolutionary algorithm, namely a genetic algorithm, the scope of the methods for this technology is not limited to genetic algorithms. Indeed, the scope of the present invention includes other contemplated model-based optimization techniques including, but not limited to, other evolutionary algorithms, swarm intelligence algorithms, and other optimization techniques or metaheuristic. The scope of the present invention is not limited to any particular model of a neurological disorder, such as PD. Present or future models of neurological disorders that are treated with DBS, or other electrical stimulation, are candidates for use with the methods described herein. Furthermore, while certain electrical stimulation patterns have been clinically applied in an effort to quantify their efficacy and efficiency, it will be appreciated that the scope of the present invention is not necessarily limited to any particular stimulation pattern as disclosed, but rather the scope of the present invention encompasses all patterns generated according hereto. The claims as follows are intended to include all modifications and alterations insofar as they come within the scope of the claims or the equivalent thereof

Having thus described the invention, the following is claimed:

1. A method for stimulation of a targeted neurological tissue region comprising the steps of:
developing a first temporal pattern of stimulation using a model-based optimization technique to suppress pathological oscillatory activity in the basal ganglia, wherein the model-based optimization technique comprises a genetic algorithm or swarm intelligence algorithm to reduce at least one model-based measurement that serves as a proxy for a motor symptom of the animal; and
applying electrical current to a targeted neurological tissue region of the animal using an implantable pulse generator according to the first temporal pattern of stimulation, which comprises a repeating succession of a non-regular pulse train comprising a plurality of pulses having non-regular, differing inter-pulse intervals therebetween.

2. The method of claim 1 further comprising the steps of:
utilizing the model-based optimization technique to determine a second temporal pattern of stimulation, the second temporal pattern of stimulation comprising a repeating succession of a non-regular pulse train comprising a plurality of pulses having non-regular, non-random, differing inter-pulse intervals therebetween; and
applying electrical current to the targeted neurological tissue region of the animal using the pulse generator according to the second temporal pattern of stimulation to reduce at least one motor symptom of a neurological disease or disorder of the animal.

3. The method of claim 2 further comprising repeating the applying electrical current to the targeted neurological tissue region of the animal using the pulse generator according to the second temporal pattern of stimulation in succession, wherein the second temporal pattern of stimulation is different from the first temporal pattern of stimulation.

4. The method of claim 2 further comprising obtaining results of the first temporal pattern of stimulation or second temporal pattern of stimulation and utilizing a computer model to analyze results of the first temporal pattern of stimulation or second temporal pattern of stimulation.

5. The method of claim 4, wherein analyzing results of the first temporal pattern of stimulation comprises quantitatively assessing the first temporal pattern of stimulation having an average frequency and at least one model-based measurement that serves as a proxy for a motor symptom of the animal.

6. The method of claim 5, wherein analyzing results of the first temporal pattern of stimulation includes applying a cost function for the first temporal pattern of stimulation based upon the at least one model-based measurement that serves as a proxy for a motor symptom of the animal and frequency, the cost function weighting the at least one model-based measurement and frequency to minimize the at least one model-based measurement and frequency.

7. The method of claim 6, wherein analyzing results of the first temporal pattern of stimulation includes calculating the cost function to evaluate the cost of the first temporal pattern of stimulation.

8. The method of claim 2, wherein the second temporal pattern of stimulation reduces the at least one motor symptom of the neurological disease or disorder of the animal more than the first temporal pattern of stimulation.

9. The method of claim 8, wherein the at least one motor symptom of the neurological disease or disorder is tremor.

* * * * *